(12) United States Patent
Chen et al.

(10) Patent No.: US 8,124,389 B2
(45) Date of Patent: Feb. 28, 2012

(54) CRYSTAL STRUCTURE OF ALDEHYDE DEHYDROGENASE AND METHODS OF USE THEREOF

(75) Inventors: Che-Hong Chen, Fremont, CA (US); Daria Mochly-Rosen, Menlo Park, CA (US); Thomas D. Hurley, Indianapolis, ID (US)

(73) Assignees: The Board of Trustees of the Leland Stanford Junior University, Palo Alto, CA (US); Indiana University Research and Technology Corporation, Indianapolis, IN (US)

( * ) Notice: Subject to any disclaimer, the term of this patent is extended or adjusted under 35 U.S.C. 154(b) by 101 days.

(21) Appl. No.: 12/435,265

(22) Filed: May 4, 2009

(65) Prior Publication Data

US 2009/0280516 A1 Nov. 12, 2009

Related U.S. Application Data

(60) Provisional application No. 61/126,890, filed on May 7, 2008.

(51) Int. Cl.
*C12N 9/04* (2006.01)
(52) U.S. Cl. ........................................ 435/190
(58) Field of Classification Search .................. None
See application file for complete search history.

(56) References Cited

U.S. PATENT DOCUMENTS

2008/0201123 A1* 8/2008 Cosgrove ...................... 703/11

OTHER PUBLICATIONS

Larson et al., J. Biol. Chem. 280:30550-30556, 2005.*
Zheng et al., Alchol. Clin. Exp. Res. 17:828-831, 1993.*
GenPept Accession No. P05091, Feb. 1991, 3 pages.*
Didierjean et al., J. Biol. Chem. 278:12968-12976, 2003.*
Perez-Miller et al., "Conformational Selection of Coenzyme Bound to Human Mitochondrial Aldehyde Dehydrogenase", Dissertation, Indiana University, 2005.*
Perez-Miller and Hurley. Coenzyme Isomerization is Integral to Catalysis in Aldehyde Dehydrogenase. (2003) Biochem. 42:7100.
Larson et al. Disruption of the coenzyme binding site and dimer interface revealed in the crystal structure of mitochondrial aldehyde dehydrogenase 'Asian' variant. (2005) J. Biol. Chem. 280:30550.
Li et al. Mitochondrial aldehyde dehydrogenase-2 (ALDH2) Glu504Lys polymorphism contributes to the variation in efficacy of sublingual nitroglycerin. (2006) J. Clin. Invest. 116:506.
Larson, et al. Structural and functional consequences of coenzyme binding to the inactive asian variant of mitochondrial aldehyde dehydrogenase: roles of residues 475 and 487. J Biol Chem. Apr. 27, 2007;282(17):12940-50.
Chen, et al. Activation of aldehyde dehydrogenase-2 reduces ischemic damage to the heart. Science. Sep. 12, 2008;321(5895):1493-5.
Lorentzen, et al. Structural Basis of allosteric regulation and substrate specificity of the non-phosphorylating glyceraldehyde 3-Phosphate dehydrogenase from Thermoproteus tenax. J Mol Biol. Aug. 13, 2004;341(3):815-28.

* cited by examiner

*Primary Examiner* — David J Steadman
(74) *Attorney, Agent, or Firm* — Paula A. Borden; Bozicevic, Field & Francis LLP.

(57) ABSTRACT

The present disclosure provides a crystal structure of aldehyde dehydrogenase (ALDH) with a modulator of ALDH bound thereto. The present disclosure provides a computer readable medium comprising atomic coordinates for an ALDH polypeptide and a modulator bound to a site within the polypeptide. A method is also provided. In general terms, the method comprises computationally identifying a compound that binds to an ALDH polypeptide, using the atomic coordinates.

6 Claims, 11 Drawing Sheets

```
  1 mlraaarfgp rlgrrllsaa atqavpapnq qpevfcnqif innewhdavs rktfptvnps
 61 tgevicqvae gdkedvdkav kaaraafqlg spwrrmdash rgrllnrlad lierdrtyla
121 aletldngkp yvisylvdld mvlkclryya gwadkyhgkt ipidgdffsy trhepvgvcg
181 qiipwnfpll mqawklgpal atgnvvvmkv aeqtpltaly vanlikeagf ppgvvnivpg
241 fgptagaaia shedvdkvaf tgsteigrvi qvaagssnlk rvtlelggks pniimsdadm
301 dwaveqahfa lffnqgqccc agsrtfvqed iydefversv araksrvvgn pfdskteqgp
361 qvdetqfkki lgyintgkqe gaklicgggi aadrgyfiqp tvfgdvqdgm tiakeeifgp
421 vmqilkfkti eevvgranns tyglaaavft kdldkanyls qalqagtvwv ncydvfgaqs
481 pfggykmsgs grelgeyglq aytevktvtv kvpqkns (SEQ ID NO:1)
```

FIG. 1A

```
  1 mlraaarfgp rlgrrllsaa atqavpapnq qpevfcnqif innewhdavs rktfptvnps
 61 tgevicqvae gdkedvdkav kaaraafqlg spwrrmdash rgrllnrlad lierdrtyla
121 aletldngkp yvisylvdld mvlkclryya gwadkyhgkt ipidgdffsy trhepvgvcg
181 qiipwnfpll mqawklgpal atgnvvvmkv aeqtpltaly vanlikeagf ppgvvnivpg
241 fgptagaaia shedvdkvaf tgsteigrvi qvaagssnlk rvtlelggks pniimsdadm
301 dwaveqahfa lffnqgqccc agsrtfvqed iydefversv araksrvvgn pfdskteqgp
361 qvdetqfkki lgyintgkqe gaklicgggi aadrgyfiqp tvfgdvqdgm tiakeeifgp
421 vmqilkfkti eevvgranns tyglaaavft kdldkanyls qalqagtvwv ncydvfgaqs
481 pfggykmsgs grelgeyglq aytkvktvtv kvpqkns (SEQ ID NO:2)
```

FIG. 1B

SEQUENCE LISTING

<160> NUMBER OF SEQ ID NOS: 3

<210> SEQ ID NO 1
<211> LENGTH: 517
<212> TYPE: PRT
<213> ORGANISM: Homo sapiens

<400> SEQUENCE: 1

```
Met Leu Arg Ala Ala Ala Arg Phe Gly Pro Arg Leu Gly Arg Arg Leu
 1               5                  10                  15

Leu Ser Ala Ala Ala Thr Gln Ala Val Pro Ala Pro Asn Gln Gln Pro
             20                  25                  30

Glu Val Phe Cys Asn Gln Ile Phe Ile Asn Asn Glu Trp His Asp Ala
         35                  40                  45

Val Ser Arg Lys Thr Phe Pro Thr Val Asn Pro Ser Thr Gly Glu Val
     50                  55                  60

Ile Cys Gln Val Ala Glu Gly Asp Lys Glu Asp Val Asp Lys Ala Val
 65                  70                  75                  80

Lys Ala Ala Arg Ala Ala Phe Gln Leu Gly Ser Pro Trp Arg Arg Met
                 85                  90                  95

Asp Ala Ser His Arg Gly Arg Leu Leu Asn Arg Leu Ala Asp Leu Ile
            100                 105                 110

Glu Arg Asp Arg Thr Tyr Leu Ala Ala Leu Glu Thr Leu Asp Asn Gly
        115                 120                 125

Lys Pro Tyr Val Ile Ser Tyr Leu Val Asp Leu Asp Met Val Leu Lys
    130                 135                 140

Cys Leu Arg Tyr Tyr Ala Gly Trp Ala Asp Lys Tyr His Gly Lys Thr
145                 150                 155                 160

Ile Pro Ile Asp Gly Asp Phe Phe Ser Tyr Thr Arg His Glu Pro Val
                165                 170                 175

Gly Val Cys Gly Gln Ile Ile Pro Trp Asn Phe Pro Leu Leu Met Gln
            180                 185                 190

Ala Trp Lys Leu Gly Pro Ala Leu Ala Thr Gly Asn Val Val Val Met
        195                 200                 205

Lys Val Ala Glu Gln Thr Pro Leu Thr Ala Leu Tyr Val Ala Asn Leu
    210                 215                 220

Ile Lys Glu Ala Gly Phe Pro Pro Gly Val Val Asn Ile Val Pro Gly
225                 230                 235                 240

Phe Gly Pro Thr Ala Gly Ala Ala Ile Ala Ser His Glu Asp Val Asp
                245                 250                 255

Lys Val Ala Phe Thr Gly Ser Thr Glu Ile Gly Arg Val Ile Gln Val
            260                 265                 270

Ala Ala Gly Ser Ser Asn Leu Lys Arg Val Thr Leu Glu Leu Gly Gly
        275                 280                 285

Lys Ser Pro Asn Ile Ile Met Ser Asp Ala Asp Met Asp Trp Ala Val
    290                 295                 300

Glu Gln Ala His Phe Ala Leu Phe Phe Asn Gln Gly Gln Cys Cys Cys
305                 310                 315                 320

Ala Gly Ser Arg Thr Phe Val Gln Glu Asp Ile Tyr Asp Glu Phe Val
                325                 330                 335
```

Glu Arg Ser Val Ala Arg Ala Lys Ser Arg Val Val Gly Asn Pro Phe
            340                 345                 350

Asp Ser Lys Thr Glu Gln Gly Pro Gln Val Asp Glu Thr Gln Phe Lys
            355                 360                 365

Lys Ile Leu Gly Tyr Ile Asn Thr Gly Lys Gln Glu Gly Ala Lys Leu
            370                 375                 380

Leu Cys Gly Gly Gly Ile Ala Ala Asp Arg Gly Tyr Phe Ile Gln Pro
385                 390                 395                 400

Thr Val Phe Gly Asp Val Gln Asp Gly Met Thr Ile Ala Lys Glu Glu
            405                 410                 415

Ile Phe Gly Pro Val Met Gln Ile Leu Lys Phe Lys Thr Ile Glu Glu
            420                 425                 430

Val Val Gly Arg Ala Asn Asn Ser Thr Tyr Gly Leu Ala Ala Ala Val
            435                 440                 445

Phe Thr Lys Asp Leu Asp Lys Ala Asn Tyr Leu Ser Gln Ala Leu Gln
            450                 455                 460

Ala Gly Thr Val Trp Val Asn Cys Tyr Asp Val Phe Gly Ala Gln Ser
465                 470                 475                 480

Pro Phe Gly Gly Tyr Lys Met Ser Gly Ser Gly Arg Glu Leu Gly Glu
            485                 490                 495

Tyr Gly Leu Gln Ala Tyr Thr Glu Val Lys Thr Val Thr Val Lys Val
            500                 505                 510

Pro Gln Lys Asn Ser
            515

<210> SEQ ID NO 2
<211> LENGTH: 517
<212> TYPE: PRT
<213> ORGANISM: Homo sapiens

<400> SEQUENCE: 2

Met Leu Arg Ala Ala Ala Arg Phe Gly Pro Arg Leu Gly Arg Arg Leu
1               5                   10                  15

Leu Ser Ala Ala Ala Thr Gln Ala Val Pro Ala Pro Asn Gln Gln Pro
            20                  25                  30

Glu Val Phe Cys Asn Gln Ile Phe Ile Asn Asn Glu Trp His Asp Ala
            35                  40                  45

Val Ser Arg Lys Thr Phe Pro Thr Val Asn Pro Ser Thr Gly Glu Val
        50                  55                  60

Ile Cys Gln Val Ala Glu Gly Asp Lys Glu Asp Val Asp Lys Ala Val
65                  70                  75                  80

Lys Ala Ala Arg Ala Ala Phe Gln Leu Gly Ser Pro Trp Arg Arg Met
            85                  90                  95

Asp Ala Ser His Arg Gly Arg Leu Leu Asn Arg Leu Ala Asp Leu Ile
            100                 105                 110

Glu Arg Asp Arg Thr Tyr Leu Ala Ala Leu Glu Thr Leu Asp Asn Gly
            115                 120                 125

Lys Pro Tyr Val Ile Ser Tyr Leu Val Asp Leu Asp Met Val Leu Lys
            130                 135                 140

Cys Leu Arg Tyr Tyr Ala Gly Trp Ala Asp Lys Tyr His Gly Lys Thr
145                 150                 155                 160

Ile Pro Ile Asp Gly Asp Phe Phe Ser Tyr Thr Arg His Glu Pro Val
            165                 170                 175

Gly Val Cys Gly Gln Ile Ile Pro Trp Asn Phe Pro Leu Leu Met Gln
            180                 185                 190

```
Ala Trp Lys Leu Gly Pro Ala Leu Ala Thr Gly Asn Val Val Met
        195                 200                 205

Lys Val Ala Glu Gln Thr Pro Leu Thr Ala Leu Tyr Val Ala Asn Leu
210                 215                 220

Ile Lys Glu Ala Gly Phe Pro Pro Gly Val Val Asn Ile Val Pro Gly
225                 230                 235                 240

Phe Gly Pro Thr Ala Gly Ala Ile Ala Ser His Glu Asp Val Asp
            245                 250                 255

Lys Val Ala Phe Thr Gly Ser Thr Glu Ile Gly Arg Val Ile Gln Val
            260                 265                 270

Ala Ala Gly Ser Ser Asn Leu Lys Arg Val Thr Leu Glu Leu Gly Gly
            275                 280                 285

Lys Ser Pro Asn Ile Ile Met Ser Asp Ala Asp Met Asp Trp Ala Val
            290                 295                 300

Glu Gln Ala His Phe Ala Leu Phe Phe Asn Gln Gly Gln Cys Cys Cys
305                 310                 315                 320

Ala Gly Ser Arg Thr Phe Val Gln Glu Asp Ile Tyr Asp Glu Phe Val
                325                 330                 335

Glu Arg Ser Val Ala Arg Ala Lys Ser Arg Val Val Gly Asn Pro Phe
                340                 345                 350

Asp Ser Lys Thr Glu Gln Gly Pro Gln Val Asp Glu Thr Gln Phe Lys
                355                 360                 365

Lys Ile Leu Gly Tyr Ile Asn Thr Gly Lys Gln Glu Gly Ala Lys Leu
            370                 375                 380

Leu Cys Gly Gly Gly Ile Ala Ala Asp Arg Gly Tyr Phe Ile Gln Pro
385                 390                 395                 400

Thr Val Phe Gly Asp Val Gln Asp Gly Met Thr Ile Ala Lys Glu Glu
                405                 410                 415

Ile Phe Gly Pro Val Met Gln Ile Leu Lys Phe Lys Thr Ile Glu Glu
                420                 425                 430

Val Val Gly Arg Ala Asn Asn Ser Thr Tyr Gly Leu Ala Ala Ala Val
                435                 440                 445

Phe Thr Lys Asp Leu Asp Lys Ala Asn Tyr Leu Ser Gln Ala Leu Gln
450                 455                 460

Ala Gly Thr Val Trp Val Asn Cys Tyr Asp Val Phe Gly Ala Gln Ser
465                 470                 475                 480

Pro Phe Gly Gly Tyr Lys Met Ser Gly Ser Gly Arg Glu Leu Gly Glu
                485                 490                 495

Tyr Gly Leu Gln Ala Tyr Thr Lys Val Lys Thr Val Thr Val Lys Val
            500                 505                 510

Pro Gln Lys Asn Ser
        515

<210> SEQ ID NO 3
<211> LENGTH: 17
<212> TYPE: PRT
<213> ORGANISM: Homo sapiens

<400> SEQUENCE: 3

Met Leu Arg Ala Ala Ala Arg Phe Gly Pro Arg Leu Gly Arg Arg Leu
  1               5                  10                  15

Leu
```

CRYSTAL STRUCTURE OF ALDEHYDE DEHYDROGENASE AND METHODS OF USE THEREOF

CROSS-REFERENCE

This application claims the benefit of U.S. Provisional Patent Application No. 61/126,890, filed May 7, 2008, which application is incorporated herein by reference in its entirety.

STATEMENT REGARDING FEDERALLY SPONSORED RESEARCH

The U.S. government may have certain rights in this invention, pursuant to grant nos. AA11982, AA18123, and AA11417 awarded by the National Institutes of Health.

TABLES PROVIDED IN ELECTRONIC FORM

This application includes Table 1 and Table 6. Table 1 is a text file named "STAN-595_Table_1_atomic_coordinates" created on May 4, 2009. The size of the "STAN-595_Table_1_atomic_coordinates" text file is 11,001 KB. Table 6 is a text file named "STAN-595_Table_6_atomic_coordinates" created on May 4, 2009. The size of "STAN-595_Table_6_atomic_coordinates" text file is 2,677 KB. The information contained in Table 1 and in Table 6 is hereby incorporated by reference in this application.

BACKGROUND

Aldehyde dehydrogenase (ALDH) is a family of enzymes that play a critical role in detoxification of many cytotoxic xenogenic and biogenic aldehydes. The ALDH family includes at least 11 members with different substrate specificity and cellular localization. Accumulation of cytotoxic aldehyde compounds, or defects in ALDH genes, have been implicated in a variety of diseases, including neurodegenerative diseases, cancer, myocardial infarction, stroke, and diseases related to accumulation of acetaldehyde from alcohol intake.

There is a need in the art for compounds that modulate the activity of ALDH enzymes, and for methods of rational design of such compounds.

Literature

Perez-Miller and Hurley (2003) *Biochem.* 42:7100; Larson et al. (2005) *J. Biol. Chem.* 280:30550; and Li et al. (2006) *J. Clin. Invest.* 116:506.

SUMMARY OF THE INVENTION

The present disclosure provides a crystal structure of an aldehyde dehydrogenase (ALDH) polypeptide with a modulator of ALDH bound thereto. The present disclosure provides a computer readable medium comprising atomic coordinates for an ALDH polypeptide and a modulator bound to a site within the polypeptide. A method is also provided. In general terms, the method comprises computationally identifying a compound that binds to an ALDH polypeptide, using the atomic coordinates.

Features of the Disclosure

The present disclosure provides a crystal comprising an aldehyde dehydrogenase (ALDH) polypeptide in crystalline form, where the crystal comprises a chemical entity bound to the active site of the ALDH polypeptide. In some aspects, the ALDH polypeptide is an ALDH2 polypeptide, wherein the crystal is characterized with space group $P2_1$, and has unit cell parameters of a=102 Å, b=177 Å, c=103 Å, bond angles of a=γ=90°, b=94.5°. In other aspects, the ALDH polypeptide is an ALDH2 polypeptide that comprises a Glu at a position corresponding to amino acid 504 of SEQ ID NO: 1, wherein the crystal is characterized with space group $P2_1$, and has unit cell parameters of a=102 Å, b=177 Å, c=102 Å, bond angles of a=γ=90°, b=94.6°. The bound chemical entity can be an agonist or an antagonist. In some cases, the bound entity is an agonist, where an exemplary agonist is N-(1,3-benzodioxol-5-ylmethyl)-2,6-dichlorobenzamide (also referred to herein as "Alda-1").

The ALDH polypeptide present in a subject crystal will in some cases have a length of about 500 amino acids. The ALDH polypeptide present in a subject crystal will in some cases have a length of about 500 amino acids and lack a leader peptide, e.g., amino acids 1-17 as shown in FIG. 1A. The ALDH polypeptide present in a subject crystal can comprise an amino acid sequence having at least about 80% amino acid sequence identity to amino acids 18-517 of the amino acid sequence set forth in SEQ ID NO:1, where the ALDH polypeptide comprises a Glu at a position corresponding to amino acid 504 of SEQ ID NO:1. The ALDH polypeptide present in a subject crystal can comprise an amino acid sequence having at least about 80% amino acid sequence identity to amino acids 18-517 of the amino acid sequence set forth in SEQ ID NO:1, where the ALDH polypeptide comprises a Lys at a position corresponding to amino acid 504 of SEQ ID NO:1. A subject crystal can in some embodiments diffract x-rays for a determination of structure coordinates to a resolution of between 1.5 Angstroms and 2.0 Angstroms. The present disclosure further provides a composition comprising a subject crystal.

The present disclosure provides a method involving computationally identifying a compound that binds to an ALDH polypeptide using atomic coordinates for a complex comprising the ALDH polypeptide and a ligand bound to a ligand-binding site within the ALDH polypeptide. In some embodiments, the atomic coordinates are those set forth in Table 1 or in Table 6. A subject method can further involve testing the compound to determine if it modulates an enzymatic activity of said ALDH polypeptide. A subject method can further involve testing the compound to determine if it modulates a substrate specificity of said ALDH polypeptide. In some cases, computationally identifying a compound involves employing a docking program that computationally tests known compounds for binding to said ALDH polypeptide. In some cases, computationally identifying a compound includes designing a compound that binds to said ALDH polypeptide. The compound can be designed based on a known compound.

The present disclosure provides a method that involves: a) receiving a set of atomic coordinates for a complex comprising an aldehyde dehydrogenase (ALDH) polypeptide and a ligand bound to a ligand-binding site within the ALDH polypeptide; and b) identifying a compound that binds to the ALDH polypeptide using said coordinates.

The present disclosure provides a method of identifying a drug candidate compound for the treatment of a disorder, the method generally involving: a) employing the three-dimensional structural coordinates of an ALDH polypeptide and determining the binding mode of a test compound within the catalytic site of the ALDH polypeptide; b) selecting a test compound having the best fit with the ALDH catalytic site; and c) assaying the ability of the test compound to modulate ALDH catalytic activity, wherein a test compound that modulates ALDH catalytic activity is considered a candidate agent for treating a disorder. In some embodiments, where the test agent blocks access of a substrate to one or both of Cys 302 and Glu 268 of the active site, and the test agent reduces catalytic activity of the ALDH polypeptide, the test agent is considered a candidate agent for treating a disorder that would benefit from reducing ALDH activity. For example, where the disorder is cancer, and the test agent is considered a candidate agent for sensitizing a cancer cell to a cancer chemotherapeutic agent. In other embodiments, where the test agent increases binding of a substrate to one or both of Cys 302 and Glu 268 of the active site, and where the test agent increases catalytic activity of the ALDH polypeptide, the test agent is considered a candidate agent for treating a disorder that would benefit from increasing ALDH activity. Examples of such disorders include a disorder resulting from a toxic level of an aldehyde, cataract, oral cancer, esophageal cancer, an upper digestive tract cancer, lung cancer, atopic dermatitis, radiation dermatitis, an acute or chronic ischemic or oxidative stress disease, nitroglycerin insensitivity, seizure, and a neurodegenerative disease.

The present disclosure provides computer-assisted method for identifying potential modulators of aldehyde dehydrogenase (ALDH), using a programmed computer comprising a processor, a data storage system, an input device, and an output device, the method involving: a) inputting into the programmed computer through said input device data comprising the three-dimensional coordinates of a subset of the atoms generated from a complex of ALDH and an agonist or an antagonist bound at or near the active site of the ALDH, thereby generating a criteria data set; b) comparing, using the processor, the criteria data set to a computer database of chemical structures stored in the computer data storage system; c) selecting from the database, using computer methods, chemical structures having a portion that is structurally similar to the criteria data set; and d) outputting to the output device the selected chemical structures having a portion similar to the criteria data set.

The present disclosure provides a computer readable medium comprising atomic coordinates for a complex comprising: i) an aldehyde dehydrogenase (ALDH) polypeptide; and ii) a ligand bound to a ligand-binding site in the ALDH polypeptide. A subject computer readable medium can further include programming for displaying a molecular model of said ALDH polypeptide. A subject computer readable medium can further include programming for identifying a compound that binds to said ALDH polypeptide. A subject computer readable medium can further include a database of structures of known test compounds. In some embodiments, the atomic coordinates present in a subject computer-readable medium are those set forth in Table 1. In some embodiments, the atomic coordinates present in a subject computer-readable medium are those set forth in Table 6.

The present disclosure provides a computer comprising a subject computer-readable medium.

The present disclosure provides a computer system comprising: a memory comprising X-ray crystallographic structure coordinates defining a ligand-binding site of a complex comprising an ALDH polypeptide with a ligand bound to a ligand-binding site within the ALDH polypeptide; and a processor in electrical communication with the memory; where the processor generates a molecular model having a three dimensional structure representative of at least a portion of the ALDH polypeptide-bound ligand complex.

BRIEF DESCRIPTION OF THE DRAWINGS

FIG. 1A and FIG. 1B provide the amino acid sequence of an E487K variant of human ALDH2 (SEQ ID NO:1) and the amino acid sequence of "wild-type" human ALDH2 (SEQ ID NO:2), respectively.

DEFINITIONS

Figure 2:
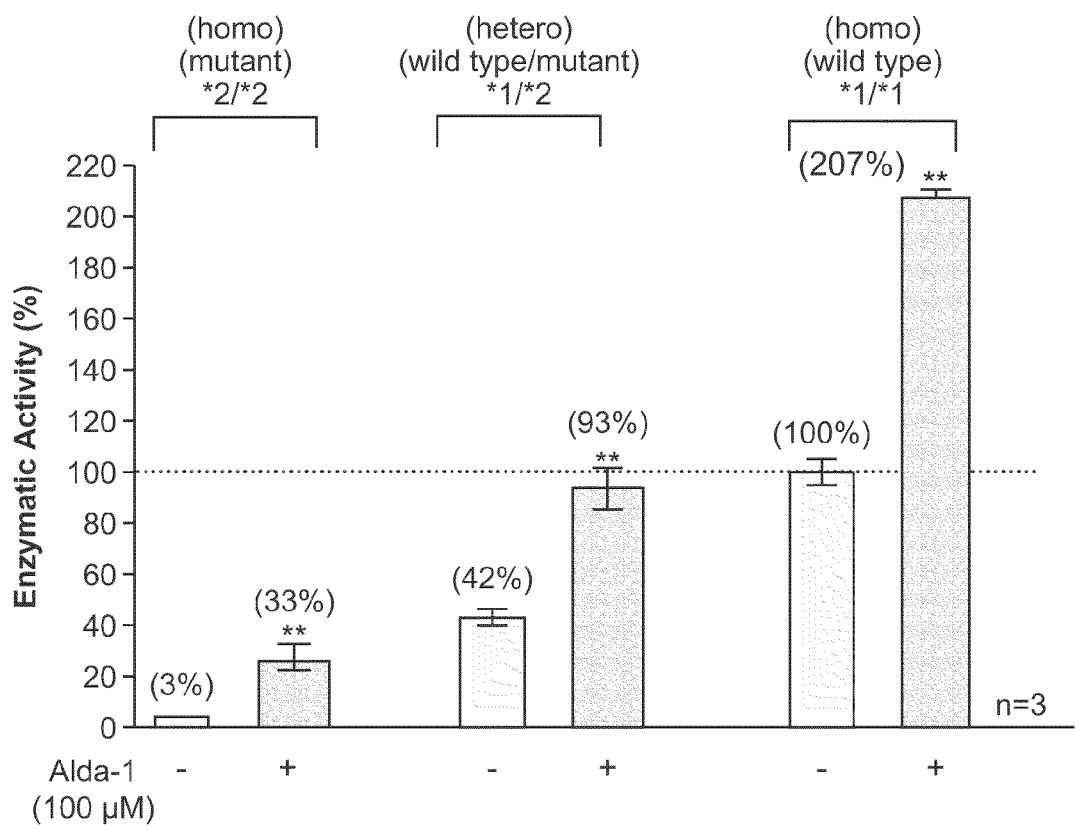
FIG. 2 depicts enzyme activation of homotetrameric wild type ALDH2 (homo wild type), heterotetrameric ALDH2 (hetero wild type/mutant; comprising a mixture of wild-type and mutant monomers), and homotetrameric mutant ALDH2 by Alda-1(100 μM). Enzymatic activity of recombinant ALDH2 proteins (20 μg each) is presented in percentage using homotetrameric wild type enzyme as a 100% control (n=3, **p<0.01 vs. control).

As used herein, the term "binding site" or "binding pocket" refers to a region of a polypeptide (e.g., an ALDH polypeptide) that binds or interacts with a particular compound.

As used herein, the term "interface" refers to the point or surface at which two or more domains of one or more molecules associate.

As used herein, the terms "associates with" or "interacts with" refers to a condition of proximity between a chemical entity, compound, or portions thereof, with another chemical entity, compound or portion thereof. The association or interaction may be non-covalent—wherein the juxtaposition is energetically favored by hydrogen bonding or van der Waals or electrostatic interactions—or it may be covalent.

As used herein, the term "pharmacophore" refers to an ensemble of steric and electronic features that is necessary to ensure the optimal supramolecular interactions with a specific biological target structure and to trigger or block a biological response. A pharmacophore may be used to design one or more candidate compounds that comprise all or most of the ensemble of steric and electronic features present in the pharmacophore and that are expected to bind to a site and trigger or block a biological response.

Structural similarity may be inferred from, e.g., sequence similarity, which can be determined by one of ordinary skill through visual inspection and comparison of the sequences, or through the use of well-known alignment software programs such as CLUSTAL (Wilbur, W. J. and Lipman, D. J. Proc. Natl. Acad. Sci. USA, 80, 726-730 (1983)) or CLUSTALW (Thompson, J. D., Higgins, D. G. and Gibson, T. J., CLUSTAL W: improving the sensitivity of progressive multiple sequence alignment through sequence weighting, positions-specific gap penalties and weight matrix choice, Nucleic Acids Research, 22:4673-4680 (1994)) or BLAST (Altschul S F, Gish W, et al., .J Mol. Biol., October 5;215(3): 403-10 (1990)), a set of similarity search programs designed to explore all of the available sequence databases regardless of whether the query is protein or DNA. CLUSTAL W is available on the internet at ebi.ac.uk/clustalw/; BLAST is available on the internet at ncbi.nlm.nih.gov/BLAST/. A residue within a first protein or nucleic acid sequence corresponds to a residue within a second protein or nucleic acid sequence if the two residues occupy the same position when the first and second sequences are aligned.

The term "atomic coordinates" refers to the Cartesian coordinates corresponding to an atom's spatial relationship to other atoms in a molecule or molecular complex. Atomic coordinates may be obtained using x-ray crystallography techniques or nuclear magnetic resonance techniques, or may be derived using molecular replacement analysis or homology modeling. Various software programs allow for the graphical representation of a set of structural coordinates to obtain a three dimensional representation of a molecule or molecular complex. The atomic coordinates of the present disclosure may be modified from the original set provided in Table 1 or Table 6 by mathematical manipulation, such as by inversion or integer additions or subtractions. As such, it is recognized that the structural coordinates of the present invention are relative, and are in no way specifically limited by the actual x, y, z coordinates of Table 1 or Table 6.

"Root mean square deviation" is the square root of the arithmetic mean of the squares of the deviations from the mean, and is a way of expressing deviation or variation from the structural coordinates described herein. The present disclosure includes all embodiments comprising conservative substitutions of the noted amino acid residues resulting in same structural coordinates within the stated root mean square deviation. It will be apparent to the skilled practitioner that the numbering of the amino acid residues of ALDH may be different than that set forth herein, and may contain certain conservative amino acid substitutions that yield the same three dimensional structures as those defined by Table 1 or Table 6. Corresponding amino acids and conservative substitutions in other isoforms or analogues are easily identified by visual inspection of the relevant amino acid sequences or by using commercially available homology software programs (e.g., MODELLER, Accelrys, San Diego, Calif.; Sali and Blundell (1993) *J Mol Biol* 234:779-815; Sanchez and Sali (1997) *Curr Opin Struct Biol* 7: 206-214; and Sanchez and Sali (1998) *Proc Natl Acad Sci USA* 95: 13597-13602).

The terms "system" and "computer-based system" refer to the hardware means, software means, and data storage means used to analyze the information of the present disclosure. The minimum hardware of the computer-based systems of the present invention comprises a central processing unit (CPU), input means, output means, and data storage means. As such, any convenient computer-based system may be employed in the present disclosure. The data storage means may comprise any manufacture comprising a recording of the present information as described above, or a memory access means that can access such a manufacture.

A "processor" references any hardware and/or software combination which will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

"Computer readable medium" as used herein refers to any storage or transmission medium that participates in providing instructions and/or data to a computer for execution and/or processing. Examples of storage media include floppy disks, magnetic tape, USB, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer. A file may be stored in permanent memory.

With respect to computer readable media, "permanent memory" refers to memory that is permanently stored on a data storage medium. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

To "record" data, programming or other information on a computer readable medium refers to a process for storing information, using any convenient method. Any convenient data storage structure may be chosen, based on the means used to access the stored information. A variety of data processor programs and formats can be used for storage, e.g. word processing text file, database format, etc.

A "memory" or "memory unit" refers to any device which can store information for subsequent retrieval by a processor, and may include magnetic or optical devices (such as a hard disk, floppy disk, CD, or DVD), or solid state memory devices (such as volatile or non-volatile RAM). A memory or memory unit may have more than one physical memory device of the same or different types (for example, a memory may have multiple memory devices such as multiple hard drives or multiple solid state memory devices or some combination of hard drives and solid state memory devices).

A system can include hardware components which take the form of one or more platforms, e.g., in the form of servers, such that any functional elements of the system, i.e., those elements of the system that carry out specific tasks (such as managing input and output of information, processing information, etc.) of the system may be carried out by the execution of software applications on and across the one or more computer platforms represented of the system. The one or more platforms present in the subject systems may be any convenient type of computer platform, e.g., such as a server, main-frame computer, a work station, etc. Where more than one platform is present, the platforms may be connected via any convenient type of connection, e.g., cabling or other communication system including wireless systems, either networked or otherwise. Where more than one platform is present, the platforms may be co-located or they may be physically separated. Various operating systems may be employed on any of the computer platforms, where representative operating systems include Windows, MacOS, Sun Solaris, Linux, OS/400, Compaq Tru64 Unix, SGI IRIX, Siemens Reliant Unix, and others. The functional elements of system may also be implemented in accordance with a variety of software facilitators, platforms, or other convenient method.

Items of data are "linked" to one another in a memory when the same data input (for example, filename or directory name or search term) retrieves the linked items (in a same file or not) or an input of one or more of the linked items retrieves one or more of the others.

Subject computer readable media may be at a "remote location", where "remote location," means a location other than the location at which the x-ray crystallographic or other analysis is carried out. For example, a remote location could be another location (e.g., office, lab, etc.) in the same city, another location in a different city, another location in a different state, another location in a different country, etc. As such, when one item is indicated as being "remote" from another, what is meant is that the two items may be in the same room but separated, or at least in different rooms or different buildings, and may be at least one mile, ten miles, or at least one hundred miles apart.

"Communicating" information references transmitting the data representing that information as, e.g., electrical or optical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the Internet or Intranets including email transmissions and information recorded on websites and the like.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an aldehyde dehydrogenase polypeptide" includes a plurality of such polypeptides and reference to "the x-ray structure" includes reference to one or more x-ray structures and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a crystal of an aldehyde dehydrogenase (ALDH) polypeptide with a modulator of ALDH bound thereto. The present disclosure provides a crystal structure of aldehyde dehydrogenase (ALDH) with a modulator of ALDH bound thereto. The present disclosure also provides a computer readable medium comprising atomic coordinates for an ALDH polypeptide and a modulator bound to a site within the polypeptide. A subject crystal structure allows for identification and design of additional modulators of ALDH. Thus, the present disclosure provides structures and methods for identifying and designing ALDH ligands, as well as methods for studying the ALDH mechanism. Also provided is a computer system comprising: a memory comprising x-ray crystallographic structure coordinates defining a structure of an ALDH polypeptide with a bound modulator.

Crystal Structures

The present disclosure provides a crystal structure of a complex comprising an aldehyde dehydrogenase (ALDH) polypeptide and a modulator (a "ligand") of ALDH bound to the ALDH polypeptide (e.g., bound to a ligand-binding site of the ALDH polypeptide).

The terms "ALDH" and "ALDH polypeptide" are used interchangeably herein to refer to an enzyme that exhibits at least a dehydrogenase activity (e.g., dehydrogenase activity in oxidizing an aldehyde to the corresponding acid. ALDH polypeptides are known in the art, and include ALDH polypeptides from any of a variety of biological sources, including, e.g., prokaryotic sources and eukaryotic sources. Eukaryotic ALDH includes human ALDH, rodent ALDH (e.g., murine ALDH, such as mouse ALDH, and rat ALDH), ungulate ALDH (e.g., bovine, ovine, equine, etc. ALDH), and the like. A variety of ALDH polypeptides are known, and are reviewed in, e.g, Vasiliou et al. (1999) *Pharmacogenetics* 9:421; Sophos et al. (2001) *Chemico-Biological Interactions* 130-132:323-337; Sophos and Vasiliou (2003) *Chem. Biol. Interact.* 143-144:5-22; and Vasiliou and Nebert (2005) *Hum. Genomics* 2:138-143. The term "ALDH" includes and ALDH polypeptide of any ALDH family, including any isoform of ALDH.

Amino acid sequences of various human ALDH family members (e.g., "isozymes") are known in the art and are publicly available. See, e.g., GenBank Accession No. NP_000680 (ALDH 1, member A1); GenBank Accession No. NP_000684 (ALDH 1, member A3); GenBank Accession Nos. AAH02967 and NP_000681 (ALDH 2); GenBank Accession No. NP_001026976 (ALDH 3, member A2, isoform 1); GenBank Accession No. CAI39494 (ALDH 4, member A1); GenBank Accession No. CAA20248 (ALDH 5, member A1); GenBank Accession No. EAW81160 (ALDH 6, member A1, isoform CRA_b); GenBank Accession No. AAH02515 (ALDH 7, member A1); GenBank Accession No. NP_072090 (ALDH 8, member A1, isoform 1); GenBank Accession No. NP_000687 (ALDH 9, member A1); GenBank Accession No. AAG42417 (ALDH 12); GenBank Accession No. AAG42417 (ALDH 12); GenBank Accession No. NP_699160 (ALDH 16); and GenBank Accession No. CAI16766 (ALDH 18, member A1).

In some embodiments, the ALDH polypeptide component of a subject ALDH/bound ligand crystal is an ALDH2 polypeptide. The term "ALDH2" encompasses ALDH2 from various species. Amino acid sequences of ALDH2 from various species are publicly available. For example, a human ALDH2 amino acid sequence is found under GenBank Accession Nos. AAH02967 and NP_000681; a mouse ALDH2 amino acid sequence is found under GenBank Accession No. NP_033786; and a rat ALDH2 amino acid sequence is found under GenBank Accession No. NP_115792.

The term "ALDH2" as used herein encompasses wild-type ALDH2, e.g., a polypeptide comprising an amino acid sequence having at least about 75%, at least about 80%, at least about 85%, at least about 90%, at least about 95%, at least about 98%, at least about 99%, or 100%, amino acid sequence identity to amino acids 18-517 of the amino acid sequence set forth in SEQ ID NO:2, and having a Lys at position 487 of mature ALDH2 (e.g., ALDH2 lacking amino acids 1-17 as set forth in SEQ ID NO:2), and having at least about 75%, at least about 80%, at least about 85%, at least about 90%, at least about 95%, at least about 98%, at least about 99%, or 100%, of the enzymatic activity of a polypeptide comprising amino acids 18-517 of SEQ ID NO:2. In some embodiments, a wild-type ALDH2 polypeptide lacks the MLRAAARFGPRLGRRLL (SEQ ID NO:3) peptide depicted in FIG. 1B, and has a length of about 500 amino acids. In some embodiments, a wild-type ALDH2 polypeptide comprises amino acids 18-517 of SEQ ID NO:2. Wild-type ALDH2 having the sequence of amino acids 18-517 of SEQ ID NO:2 is sometimes referred to herein as "wild-type ALDH2" or "ALDH2*1."

The term "ALDH2" as used herein also encompasses fragments, fusion proteins, and variants (e.g., variants having one or more amino acid substitutions, addition, deletions, and/or insertions) that retain ALDH2 enzymatic activity. Specific enzymatically active ALDH2 variants, fragments, fusion proteins, and the like can be verified by adapting the methods described herein. An example of an ALDH2 variant is an ALDH2 polypeptide that comprises a Glu-to-Lys substitution at amino acid position 487 of mature human ALDH2, as depicted in FIG. 1A (amino acid 504 of SEQ ID NO:1), at a position corresponding to amino acid 487 of mature human ALDH2, or at a position corresponding to amino acid 504 of SEQ ID NO:1). This mutation is referred to as the "E487K mutation"; the "E487K variant"; or as the "Glu504Lys polymorphism". See, e.g., Larson et al. (2005) *J. Biol. Chem.* 280:30550; and Li et al. (2006) *J. Clin. Invest.* 116:506. An ALDH2 variant retains at least about 1% of the enzymatic activity of a corresponding wild-type ALDH2 enzyme. For example, the E487K variant retains at least about 1% of the activity of an enzyme comprising the amino acid sequence depicted in FIG. 1B (SEQ ID NO:2). An ALDH2 polypeptide can have a length of about 500 amino acids, and can lack the MLRAAARFGPRLGRRLL (SEQ ID NO:3) peptide depicted in FIGS. 1A and 1B. An E487K variant of ALDH2 can have the amino acid sequence of amino acids 18-517 of SEQ ID NO:1, can have a length of about 500 amino acids, and can lack the MLRAAARFGPRLGRRLL (SEQ ID NO:3) peptide depicted in FIG. 1A; such an E487K variant of ALDH2 is sometimes referred to herein as ALDH2*2. In some embodiments, an E487K variant of ALDH2 can have the amino acid sequence of amino acids 18-517 of SEQ ID NO: 1, except for having an S302 mutation (e.g., a change from Cys to Ser at amino acid 319 of the sequence depicted in FIG. 1A; see, e.g., Perez-Miller and Hurley (2003) *Biochem.* 42:7100), can have a length of about 500 amino acids, and can lack the MLRAAARFGPRLGRRLL (SEQ ID NO:3) peptide depicted in FIG. 1A.

The term "ALDH2" encompasses an enzymatically active polypeptide having at least about 75%, at least about 80%, at least about 85%, at least about 90%, at least about 95%, at least about 98%, at least about 99%, or 100%, amino acid sequence identity to amino acids 18-517 of the amino acid sequence set forth in SEQ ID NO:1 or SEQ ID NO:2. The term "ALDH2" encompasses an enzymatically active polypeptide having at least about 75%, at least about 80%, at least about 85%, at least about 90%, at least about 95%, at least about 98%, at least about 99%, or 100%, amino acid sequence identity to amino acids 18-517 of the amino acid sequence set forth in SEQ ID NO:1, where the amino acid sequence at a position corresponding to amino acid 504 of SEQ ID NO:1 is a Glu. The term "ALDH2" encompasses an enzymatically active polypeptide having at least about 75%, at least about 80%, at least about 85%, at least about 90%, at least about 95%, at least about 98%, at least about 99%, or 100%, amino acid sequence identity to amino acids 18-517 of the amino acid sequence set forth in SEQ ID NO:1, where the amino acid sequence at a position corresponding to amino acid 504 of SEQ ID NO:1 is a Lys.

The term "ALDH" encompasses a polypeptide having a length of from about 400 amino acids to about 600 amino acids (aa), e.g., from about 400 aa to about 450 aa, from about 450 aa to about 500 aa, from about 500 aa to about 550 aa, or from about 550 aa to about 600 aa.

An ALDH polypeptide can exhibit one or more of the following enzymatic activities: a) a dehydrogenase activity (e.g., dehydrogenase activity in oxidizing an aldehyde (e.g., a xenogenic aldehyde, a biogenic aldehyde, or an aldehyde produced from a compound that is ingested, inhaled, or absorbed) to the corresponding acid); b) an esterase activity; and c) a reductase activity.

The X-ray crystal structures described herein are useful as models for rationally designing pharmacophores and/or candidate compounds, either de novo or by modification of known compounds. Pharmacophores and candidate compounds identified through the use of the crystal structure coordinates are useful for altering the enzymatic activity and/or substrate selectivity of an ALDH polypeptide, and so have utility for treating a variety of disorders related to ALDH activity. Pharmacophores and candidate compounds may be determined according to any method known in the art, including the methods described herein.

Crystals and Crystal Compositions

The present disclosure provides crystals that include an ALDH polypeptide and a chemical entity (e.g., an agonist or an antagonist) bound to a binding site of the ALDH polypeptide. In some embodiments, the crystal is capable of diffracting x-rays at a resolution of less than 5 Angstroms, less than 4 Angstroms, less than 3 Angstroms, or less than 2 Angstroms. For example, in some embodiments, a subject crystal is capable of diffracting x-rays at a resolution of between 1.5 Angstroms and 2.0 Angstroms. For example, in some embodiments, a subject crystal is capable of diffracting x-rays at a resolution of 1.69 Angstroms. In some embodiments, a subject crystal has a unit cell dimension of a=102 Å, b=177 Å, c=103 Å, with bond angles a=γ=90°, b=94.5°, and belongs to space group $P2_1$. As another example, in some embodiments, a subject crystal is capable of diffracting x-rays at a resolution of 1.9 Angstroms. In some embodiments, a subject crystal has a unit cell dimension of a=102 Å, b=177 Å, c=102 Å, with bond angles a=γ=90°, b=94.6°, and belongs to space group $P2_1$. A subject crystal can have atomic coordinates as presented in Table 1 or Table 6, or similar coordinates.

The present disclosure also provides a composition comprising a subject crystal.

In some embodiments, the chemical entity bound to the ALDH polypeptide is an ALDH agonist. In some embodiments, the chemical entity bound to the ALDH polypeptide is an ALDH antagonist. In some embodiments, the chemical entity is bound to the ALDH polypeptide Alda-1 (N-(1,3-benzodioxol-5-ylmethyl)-2,6-dichlorobenzamide).

In some embodiments, the ALDH polypeptide comprises an amino acid sequence having at least about 75%, at least about 80%, at least about 85%, at least about 90%, at least about 95%, at least about 98%, at least about 99%, or 100%, amino acid sequence identity to amino acids 18-517 of the amino acid sequence set forth in SEQ ID NO:1 or SEQ ID NO:2. In some embodiments, the ALDH polypeptide comprises an amino acid sequence having at least about 75%, at least about 80%, at least about 85%, at least about 90%, at least about 95%, at least about 98%, at least about 99%, or 100%, amino acid sequence identity to amino acids 18-517 of the amino acid sequence set forth in SEQ ID NO:1, where the amino acid sequence at a position corresponding to amino acid 504 of SEQ ID NO: 1 is a Glu. In some embodiments, the ALDH polypeptide comprises an amino acid sequence having at least about 75%, at least about 80%, at least about 85%, at least about 90%, at least about 95%, at least about 98%, at least about 99%, or 100%, amino acid sequence identity to amino acids 18-517 of the amino acid sequence set forth in SEQ ID NO:1, where the amino acid sequence at a position corresponding to amino acid 504 of SEQ ID NO:1 is a Lys. In some embodiments, the ALDH polypeptide comprises amino acids 18-517 of the amino acid sequence set forth in SEQ ID NO:1. In other embodiments, the ALDH polypeptide comprises amino acids 18-517 of the amino acid sequence set forth in SEQ ID NO:2.

The ALDH polypeptide can be produced using any of a variety of well known methods, including, e.g., synthetic methods, such as solid phase, liquid phase and combination solid phase/liquid phase syntheses; recombinant DNA methods, including cDNA cloning, optionally combined with site directed mutagenesis; and purification of the polypeptide from a natural source.

The present disclosure further provides a method for producing a crystal of an ALDH polypeptide and an agonist or antagonist bound in the ligand-binding site of the ALDH polypeptide. The method generally involves producing crystallizable ALDH polypeptide; forming a complex between the ALDH polypeptide and an agonist or antagonist; and obtaining a crystal from a solution comprising the ALDH/ agonist or ALDH/antagonist complex using a precipitating agent. In some embodiments, the apo-enzyme (ALDH without bound agonist or antagonist) is concentrated and equilibrated against a crystallization solution comprising a precipitating agent. A suitable crystallization solution comprising a precipitating agent is 100 mM ACES (N-(2-acetamido)-2-aminoethansulfonic acid), pH 6.4, 100 mM guanidine-HCl, 10 mM $MgCl_2$, and 16-17% (w/v) poly(ethylene glycol) (PEG) 6000. A complex of agonist or antagonist and ALDH polypeptide can be achieved by first equilibrating apo-enzyme (ALDH without agonist or antagonist) against 1% dimethylsulfoxide (DMSO) in a crystal stabilization solution (100 mM ACES, pH 6.4, 100 mM guanidine-HCl, 10 mM $MgCl_2$, and 19% (w/v) PEG 6000); allowing equilibration to proceed for 4 to 24 hours; replacing the crystal stabilization solution with crystal stabilization solution comprising an agonist or antagonist at a suitable concentration (e.g., at a concentration of from about 100 μM to about 400 μM, e.g., 200 μM); and allowing the crystals to soak for a sufficient time period in the crystal stabilization solution, thereby forming crystal complexes comprising the ALDH polypeptide and the agonist or antagonist. Crystal complexes can be soaked in a solution comprising a cryoprotectant prior to freezing in liquid $N_2$. The person skilled in the art knows that additional factors such as temperature may be crucial for crystal formation. These and other conditions of crystallization as well as strategies to optimize conditions of crystallization have been summarized in "Crystallization of Biological Macromolecules" by Alexander McPherson (Cold Spring Harbor Laboratory; 1st edition (Jan. 15, 1999).

Methods of Identifying and Designing ALDH Modulators

The present disclosure provides methods for identifying and designing ALDH ligands, as well as methods for studying the ALDH mechanism. A subject method generally involves computationally identifying a compound that binds to an ALDH polypeptide (e.g., a compound that binds to a target site (e.g., a ligand-binding site; a catalytic site; an entrance to the active site) of an ALDH polypeptide) using atomic coordinates for an ALDH polypeptide with a bound ligand. For example, in some embodiments, the atomic coordinates are those provided in Table 1. As another example, in some embodiments, the atomic coordinates are those provided in Table 6. A compound that binds to an ALDH polypeptide includes a compound that modulates (increases or decreases) enzymatic activity of the ALDH polypeptide; a compound that modulates substrate specificity/selectivity of the ALDH polypeptide; and a compound that both modulates enzymatic activity of the ALDH polypeptide and modulates substrate specificity/selectivity of the ALDH polypeptide.

The present disclosure provides a method of identifying a compound that binds to an ALDH polypeptide (e.g., to a ligand-binding site of an ALDH polypeptide; a catalytic site; an entrance to the active site), the method generally involving: designing a compound based upon a three-dimensional structure of a complex comprising an ALDH polypeptide and a ligand bound to a ligand-binding site within the ALDH polypeptide, where the three-dimensional structure is defined by structure coordinates within Table 1 or Table 6; contacting the compound with an ALDH polypeptide; and determining whether the compound binds to a ligand-binding site of the ALDH polypeptide. In some embodiments, the compound is designed de novo. In other embodiments, the compound is designed from a known compound. The compound can be an inhibitor (e.g., an antagonist) or an activator (e.g., an agonist) of an enzymatic activity of an ALDH polypeptide. In some embodiments, the compound modulates dehydrogenase activity of an ALDH polypeptide. In other embodiments, the compound modulates esterase activity of an ALDH polypeptide. In other embodiments, the compound modulates substrate specificity/selectivity of an ALDH polypeptide. In other embodiments, the compound modulate both an enzymatic activity and a substrate selectivity/specificity of an ALDH polypeptide.

In certain cases, a subject method will further comprise a testing a compound to determine if it binds and/or modulates an ALDH polypeptide, using the atomic coordinates provided herein. In some embodiments, a subject method will further comprise obtaining the compound (e.g., purchasing or synthesizing the compound) and testing the compound to determine if it modulates (e.g., activates or inhibits) an enzymatic activity of an ALDH polypeptide (e.g., acts an agonist or an antagonist of an ALDH polypeptide). In some embodiments, a subject method will further comprise obtaining the compound (e.g., purchasing or synthesizing the compound) and testing the compound to determine if it modulates substrate specificity/selectivity of an ALDH polypeptide.

In other cases, a subject method involves designing a compound that binds to an ALDH polypeptide, either de novo, or by modifying an existing compound that is known to bind to the ALDH polypeptide. In particular embodiments, a subject method involves computationally identifying a compound that binds to an ALDH polypeptide using the atomic coordinates set forth in Table 1 or Table 6. In other embodiments, a subject method involves computationally identifying a compound that binds to the ligand binding site of an ALDH polypeptide, wherein the ligand binding site includes the following amino acids: Met-124, Phe-170, Leu-173, Phe-292, Phe-296, Cys-302, and Phe-459 of human ALDH2 (or corresponding amino acids in another ALDH family member) as well as those atoms that are close thereto, e.g., within 5 Å, within 10 Å, within 20 Å or within 30 Å of those amino acids.

A method that comprises receiving a set of atomic coordinates for an ALDH polypeptide; and identifying a compound that binds to the ALDH polypeptide using the coordinates is also provided, as is a method comprising: forwarding to a remote location a set of atomic coordinates for the ALDH polypeptide; and receiving the identity of a compound that binds to the ALDH polypeptide.

In some embodiments, a subject method of identifying a compound that binds to an ALDH polypeptide (e.g., a ligand-binding site of an ALDH polypeptide), comprises the steps of: (a) providing a molecular model comprising one or more ligand-binding regions of an ALDH polypeptide, wherein the molecular model is made: (i) from the atomic co-ordinates depicted in Table 1 or Table 6; or (ii) from atomic co-ordinates derived by molecular modeling using the atomic coordinates depicted in Table 1 or Table 6; (b) using the molecular model to identify a candidate molecule that can bind to the molecular model; and (c) producing the candidate molecule identified in step (b).

A subject method can provide for one or more of: 1) improving the potency of a "lead" compound or a known compound; 2) designing new compound structures that exhibit improved structure/function relationships for ALDH modulation; 3) designing activator (agonist) compounds that are isozyme-selective activators (e.g., compounds that are selective agonists for a particular ALDH isozyme); 4) designing activator compounds that activate two or more ALDH isozymes; 5) designing inhibitor (antagonist) compounds that are isozyme-selective inhibitors (e.g., compounds that are selective inhibitors for a particular ALDH isozyme); 6) designing inhibitor compounds that inhibit two or more ALDH isozymes; 7) designing compounds that exhibit both ALDH agonist and ALDH antagonist activity; 8) designing compounds that can be directed, controlled, or switched to function as either an ALDH agonist or an ALDH antagonist; and 9) designing or selecting compounds that modulate substrate specificity of an ALDH polypeptide. Compounds that modulate substrate specificity of an ALDH polypeptide include compounds that narrow the substrate specificity of an ALDH polypeptide, e.g., such that the ALDH polypeptide demonstrates a preference, or selectivity, for short-chain, long-chain, aliphatic, or aromatic aldehyde or ester substrates; and compounds that broaden the substrate specificity of an ALDH polypeptide.

In certain embodiments, a computer system comprising a memory comprising the atomic coordinates of an ALDH polypeptide having a bound ligand (ALDH/bound ligand) is provided. The atomic coordinates are useful as models for rationally identifying compounds that a ligand binding site of an ALDH polypeptide. Such compounds may be designed either de novo, or by modification of a known compound, for example. In other cases, binding compounds may be identified by testing known compounds to determine if the "dock" with a molecular model of an ALDH polypeptide. Such docking methods are generally well known in the art.

The structure data provided herein can be used in conjunction with computer-modeling techniques to develop models of binding of various ALDH-binding compounds by analysis of the crystal structure data. The structure data provided herein can be used in conjunction with computer-modeling techniques to design compounds that modulate ALDH enzymatic activity. The site models characterize the three-dimensional topography of site surface, as well as factors including van der Waals contacts, electrostatic interactions, and hydrogen-bonding opportunities. Computer simulation techniques are then used to map interaction positions for functional groups including but not limited to protons, hydroxyl groups, amine groups, divalent cations, aromatic and aliphatic functional groups, amide groups, alcohol groups, etc. that are designed to interact with the model site. These groups may be designed into a pharmacophore or candidate compound with the expectation that the candidate compound will specifically bind to the site. Pharmacophore design thus involves a consideration of the ability of the candidate compounds falling within the pharmacophore to interact with a site through any or all of the available types of chemical interactions, including hydrogen bonding, van der Waals, electrostatic, and covalent interactions, although in general, pharmacophores interact with a site through non-covalent mechanisms.

The ability of a pharmacophore or candidate compound to bind to an ALDH polypeptide can be analyzed prior to actual synthesis using computer modeling techniques. Only those candidates that are indicated by computer modeling to bind the target (e.g., an ALDH polypeptide binding site) with sufficient binding energy (i.e., binding energy corresponding to a dissociation constant with the target on the order of $10^{-2}$ M or tighter) may be synthesized and tested for their ability to bind to an ALDH polypeptide and to modulate ALDH enzymatic function using enzyme assays known to those of skill in the art and/or as described herein. The computational evaluation step thus avoids the unnecessary synthesis of compounds that are unlikely to bind an ALDH polypeptide with adequate affinity.

An ALDH pharmacophore or candidate compound may be computationally evaluated and designed by means of a series of steps in which chemical entities or fragments are screened and selected for their ability to associate with individual binding target sites on an ALDH polypeptide. One skilled in the art may use one of several methods to screen chemical entities or fragments for their ability to associate with an ALDH polypeptide, and more particularly with target sites on an ALDH polypeptide. The process may begin by visual inspection of, for example a target site on a computer screen, based on the ALDH polypeptide coordinates, or a subset of those coordinates, as set forth in Table 1 or Table 6.

Selected fragments or chemical entities may then be positioned in a variety of orientations or "docked" within a target site of an ALDH polypeptide as defined from analysis of the crystal structure data. Manual docking may be accomplished using software such as Insight II (Accelrys, San Diego, Calif.) MOE (Chemical Computing Group, Inc., Montreal, Quebec, Canada); and SYBYL (Tripos, Inc., St. Louis, Mo., 1992), followed by energy minimization and/or molecular dynamics with standard molecular mechanics force fields, such as CHARMM (Brooks, et al., J. Comp. Chem. 4:187-217, 1983), AMBER (Weiner, et al., J. Am. Chem. Soc. 106: 765-84, 1984) and $C^2$ MMFF (Merck Molecular Force Field; Accelrys, San Diego, Calif.). More automated docking may be accomplished by using programs such as DOCK (Kuntz et al., J. Mol. Biol., 161:269-88, 1982; DOCK is available from University of California, San Francisco, Calif.); AUTODOCK (Goodsell & Olsen, Proteins: Structure, Function, and Genetics 8:195-202, 1990; AUTODOCK is available from Scripps Research Institute, La Jolla, Calif.); GOLD (Cambridge Crystallographic Data Centre (CCDC); Jones et al., J. Mol. Biol. 245:43-53, 1995); and FLEXX (Tripos, St. Louis, Mo.; Rarey, M., et al., J. Mol. Biol. 261:470-89, 1996).

Specialized computer programs may also assist in the process of selecting fragments or chemical entities. These include but are not limited to: GRID (Goodford, P. J., "A Computational Procedure for Determining Energetically Favorable Binding Sites on Biologically Important Macromolecules," J. Med. Chem., 28, pp. 849-857 (1985)); GRID is available from Oxford University, Oxford, UK; MCSS (Miranker, A. and M. Karplus, "Functionality Maps of Binding Sites: A Multiple Copy Simultaneous Search Method," Proteins: Structure, Function and Genetics, 11, pp. 29-34 (1991)); MCSS is available from Molecular Simulations, Inc., San Diego, Calif.; AUTODOCK (Goodsell, D. S. and A. J. Olsen, "Automated Docking of Substrates to Proteins by Simulated Annealing," Proteins: Structure, Function, and Genetics, 8, pp. 195-202 (1990)); AUTODOCK is available from Scripps Research Institute, La Jolla, Calif.; DOCK (Kunts, I. D., et al. "A Geometric Approach to Macromolecule-Ligand Interactions," J. Mol. Biol., 161, pp. 269-288 (1982)); DOCK is available from University of California, San Francisco, Calif.; CERIUS II (available from Accelrys, Inc., San Diego, Calif.); and Flexx (Raret, et al. J. Mol. Biol. 261, pp. 470-489 (1996)).

After selecting suitable chemical entities or fragments, they can be assembled into a single compound. Assembly may proceed by visual inspection of the relationship of the fragments to each other on a three-dimensional image of the fragments in relation to the ALDH/modulator structure or portion thereof displayed on a computer screen. Visual inspection may be followed by manual model building using software such as the Quanta or Sybyl programs described above.

Software programs also may be used to aid one skilled in the art in connecting the individual chemical entities or fragments. These include, but are not limited to CAVEAT (Bartlett, P. A., et al. "CAVEAT: A Program to Facilitate the Structure-Derived Design of Biologically Active Molecules" In "Molecular Recognition in Chemical and Biological Problems," Special Publ, Royal Chem. Soc., 78, pp. 182-196 (1989)); CAVEAT is available from the University of California, Berkeley, Calif.; 3D Database systems such as MACCS-3D (MDL Information Systems, San Leandro, Calif.); this area is reviewed in Martin, Y. C., "3D Database Searching in Drug Design," J. Med. Chem., 35:2145-2154 (1992)); and HOOK (available from Molecular Simulations Inc., San Diego, Calif.).

As an alternative to building candidate pharmacophores or candidate compounds up from individual fragments or chemical entities, they may be designed de novo using the structure of an ALDH target site, optionally, including information from co-factor(s) or known activators or inhibitor(s) that bind to the target site. De novo design may be included by programs including, but not limited to LUDI (Bohm, H. J., "The Computer Program LUDI: A New Method for the De Novo Design of Enzyme Inhibitors, J. Comp. Aid. Molec. Design, 6, pp. 61-78 (1992)); LUDI is available from Molecular Simulations, Inc., San Diego, Calif.; LEGEND (Nishibata, Y., and Itai, A., Tetrahedron 47, p. 8985 (1991); LEGEND is available from Molecular Simulations, San Diego, Calif.; and LeapFrog (available from Tripos Associates, St. Louis, Mo.).

The functional effects of known ALDH ligands also may be altered through the use of the molecular modeling and design techniques described herein. This may be carried out by docking the structure of the known ALDH ligand into an ALDH model structure and modifying the structure and charge distribution of the ligand to optimize the binding interactions with the ALDH enzyme. The modified structure may be synthesized or obtained from a library of compounds and tested for its binding affinity and/or effect on ALDH enzymatic activity. This information can be used in design of optimized ligands. The crystals and structures provided in the present disclosure are especially well suited for the docking, co-crystallization, structure-based drug design and optimization of ligands that modulate one or more enzymatic activities of an ALDH. The present disclosure permits the use of molecular, biochemical and computer modeling techniques to design and select novel ligands that interact with an ALDH and affect one or more enzymatic activities of an ALDH.

Additional molecular modeling techniques also may be employed in accordance with the invention. See, e.g., Cohen, N. C., et al. "Molecular Modeling Software and Methods for Medicinal Chemistry," J. Med. Chem., 33, pp. 883-894 (1990); Navia, M. A. and Murcko, M. A., "The Use of Structural Information in Drug Design," Curr. Opin. Biotechnol. 8, pp. 696-700 (1997); and Afshar, et al. "Structure-Based and Combinatorial Search for New RNA-Binding Drugs," Curr. Opin. Biotechnol. 10, pp. 59-63 (1999).

Following pharmacophore or candidate compound design or selection according to any of the above methods or other methods known to one skilled in the art, the efficiency with which a candidate compound falling within the pharmacophore definition binds to an ALDH polypeptide may be tested and optimized using computational evaluation. A candidate compound may be optimized, e.g., so that in its bound state it would lack repulsive electrostatic interaction with the target site. These repulsive electrostatic interactions include repulsive charge-charge, dipole-dipole, and charge-dipole interactions. In some embodiments, the sum of all electrostatic interactions between the candidate compound and an ALDH when the candidate compound is bound to the ALDH make a neutral or favorable contribution to the binding enthalpy.

Specific computer software is available in the art to evaluate compound deformation energy and electrostatic interaction. Examples of programs designed for such uses include: Gaussian 94, revision C (Frisch, Gaussian, Inc., Pittsburgh, Pa. (1995); AMBER, version 7. (Kollman, University of California at San Francisco, (2002); QUANTA/CHARMM (Accelrys, Inc., San Diego, Calif., (1995); Insight II/Discover (Accelrys, Inc., San Diego, Calif., (1995); DelPhi (Accelrys, Inc., San Diego, Calif., (1995); and AMSOL (University of Minnesota) (Quantum Chemistry Program Exchange, Indiana University). These programs may be implemented, for instance, using a computer workstation, as are well known in the art, for example, a LINUX, SGI or Sun workstation. Other hardware systems and software packages will be known to those skilled in the art.

Once a pharmacophore or candidate compound has been optimally selected or designed, as described above, substitutions may then be made in some of its atoms or side groups to improve or modify its binding properties. Generally, initial substitutions are conservative in that the replacement group will have either approximately same size, or overall structure, or hydrophobicity, or charge as the original group. Components known in the art to alter conformation should be avoided in making substitutions. Substituted candidates may be analyzed for efficiency of fit to an ALDH using the same methods described above.

Once a candidate compound has been identified using any of the methods described above, it can be screened for biological activity. Any one of a number of assays of for ALDH enzymatic activity known to those of skill in the art may be used.

Assays for dehydrogenase activity of an ALDH polypeptide are known in the art, and any known assay can be used. Examples of dehydrogenase assays are found in various publications, including, e.g., Sheikh et al. ((1997) *J. Biol. Chem.* 272:18817-18822); Vallari and Pietruszko (1984) *J. Biol. Chem.* 259:4922; and Farres et al. ((1994) *J. Biol. Chem.* 269:13854-13860).

As an example of an assay for dehydrogenase activity, ALDH2 is assayed at 25° C. in 50 mM sodium pyrophosphate HCl buffer, pH 9.0, 100 mM sodium phosphate buffer, pH 7.4, or 50 mM sodium phosphate buffer, pH 7.4, where the buffer includes $NAD^+$ (e.g., 0.8 mM $NAD^+$, or higher, e.g., 1 mM, 2 mM, or 5 mM $NAD^+$) and an aldehyde substrate such as 14 µM propionaldehyde. Reduction of $NAD^+$ is monitored at 340 nm using a spectrophotometer, or by fluorescence increase using a fluoromicrophotometer. Enzymatic activity can be assayed using a standard spectrophotometric method, e.g., by measuring a reductive reaction of the oxidized form of nicotinamide adenine dinucleotide ($NAD^+$) to its reduced form, NADH, at 340 nm, as described in US 2005/0171043; and WO 2005/057213. In an exemplary assay, the reaction is carried out at 25° C. in 0.1 $NaPP_i$ buffer, pH 9.5, 2.4 mM $NAD^+$ and 10 mM acetaldehyde as the substrate. Enzymatic activity is measured by a reductive reaction of $NAD^+$ to NADH at 340 nm, as described in US 2005/0171043; and WO 2005/057213. Alternatively, the production of NADH can be coupled with another enzymatic reaction that consumes NADH and that provides for a detectable signal. An example of such an enzymatic reaction is a diaphorase-based reaction, which reduces resazurin to its oxidized fluorescent compound resorufin, as described in US 2005/0171043; and WO 2005/057213. Detection of fluorescent resorufin at 590 nm provides amplified and more sensitive signals for any change in ALDH2 enzymatic activity.

Esterase activity of ALDH2 can be determined by monitoring the rate of p-nitrophenol formation at 400nm in 25 mM N,N-Bis (2-hydroxyethyl)-2-amino ethanesulfonic acid (BES) (pH 7.5) with 800 µM p-nitrophenyl acetate as the substrate at room temperature in the absence or presence of added $NAD^+$. A pH-dependent molar extinction coefficient of 16 $mM^{-1}$ $cm^{-1}$ at 400 nm for nitrophenol can be used. See, e.g., Larson et al. (2007) *J. Biol. Chem.* 282:12940). Esterase activity of ALDH2 can be determined by measuring the rate of p-nitrophenol formation at 400 nm in 50 mM Pipes (pH 7.4) with 1 mM p-nitrophenylacetate as the substrate. A molar extinction coefficient of $18.3 \times 10^3$ $M^{-1}$ $cm^{-1}$ at 400 nm for p-nitrophenolate can be used for calculating its rate of formation. See, e.g., Ho et al. (2005) *Biochemistry* 44:8022).

A reductase activity of an ALDH polypeptide (e.g., ALDH2) can be determined by measuring the rate of 1,2-glyceryl dinitrate and 1,3-glyceryl dinitrate formation using a thin layer chromatography (TLC) or liquid scintillation spectrometry method, using a radioactively labeled substrate. For example, 0.1 mM or 1 mM GTN (glyceryl trinitrate) is incubated with the assay mixture (1 ml) containing 100 mM KPi (pH 7.5), 0.5 mM EDTA, 1 mM NADH, 1 mM NADPH in the presence an ALDH polypeptide. After incubation at 37° C. for about 10 minutes to about 30 minutes, the reaction is stopped and GTN and its metabolites are extracted with 3×4 ml ether and pooled, and the solvent is evaporated by a stream of nitrogen. The final volume is kept to less than 100 microliter in ethanol for subsequent thin layer chromatographic (TLC) separation and scintillation counting. See, e.g., Zhang and Stamler (2002) *Proc. Natl. Acad. Sci. USA* 99:8306.

Computer Models, Computer-Readable Media, and Computer Systems

One embodiment of the present disclosure includes representations, or models, of a three dimensional structure of an ALDH with a bound ligand, such as a computer model. A computer model of the present disclosure can be produced using any suitable software program, including, but not limited to, PYMOL, GRASP, or 0 software. Suitable computer hardware useful for producing an image of the present invention are known to those of skill in the art (e.g., a Silicon Graphics Workstation, Linux PC, or MacIntosh PC).

The representations, or models, of a three dimensional structure of an ALDH with a bound ligand can also be determined based on the crystals provided in the present disclosure, with use of techniques which include molecular replacement or SIR/MIR (single/multiple isomorphous replacement). Methods of molecular replacement are generally known by those of skill in the art (generally described in Brunger, *Meth Enzym* 1997, 276:558-80; Navaza and Saludjian, *Meth Enzym* 1997, 276, 581-94; Tong and Rossmann, *Meth Enzym* 1997, 276:594-611; and Bentley, *Meth Enzym* 1997, 276:611-19, 1997, each of which is incorporated by this reference herein in its entirety) and are performed by a software program including, for example, the Phaser program (McCoy et al., *Acta Crystallogr D Biol Crystallogr* 2005, 61:458-64; Stroni et al., *Acta Crystallogr D Biol Crystallogr* 2004, 60:432-38).

Briefly, X-ray diffraction data are collected from the crystal of an ALDH having a bound ligand. The X-ray diffraction data are transformed to calculate a Patterson function. The Patterson function of the crystallized target structure is compared with a Patterson function calculated from a known structure (referred to herein as a search structure). The Patterson function of the crystallized target structure is rotated on the search structure Patterson function to determine the correct orientation of the crystallized target structure in the crystal. The translation function is then calculated to determine the location of the target structure with respect to the crystal axes. Once the crystallized target structure has been correctly positioned in the unit cell, initial phases for the experimental data can be calculated. These phases are necessary for calculation of an electron density map from which structural differences can be observed, and for refinement of the structure. Alternatively, the phases for the diffraction data can be deduced without an initial structural model through the introduction of a heavy element, such as selenium, mercury or the like. Location of the heavy atoms within the structure using their intrinsic anomalous scattering properties permits calculation of the phases for the complete structure. These methods are known to those skilled in the art. The structural features (e.g., amino acid sequence, conserved di-sulfide bonds, and β-strands or β-sheets) of the search molecule can be related to the crystallized target structure.

As used herein, the term "model" refers to a representation in a tangible medium of the three dimensional structure of an ALDH enzyme in a complex with a bound ligand. For example, a model can be a representation of the three dimensional structure in an electronic file, on a computer screen, on a piece of paper (i.e., on a two dimensional medium), and/or as a ball-and-stick figure. Physical three-dimensional models are tangible and include, but are not limited to, stick models and space-filling models. The phrase "imaging the model on a computer screen" refers to the ability to express (or represent) and manipulate the model on a computer screen using appropriate computer hardware and software technology known to those skilled in the art. Such technology is available from a variety of sources including, for example, Accelrys Inc., San Diego, Calif. The phrase "providing a picture of the model" refers to the ability to generate a "hard copy" of the model. Hard copies include both motion and still pictures. Computer screen images and pictures of the model can be visualized in a number of formats including space-filling representations, backbone traces, ribbon diagrams, and electron density maps.

One embodiment of the present disclosure relates to a computer readable medium with ALDH/bound ligand structural data and/or information stored thereon. As used herein, the phrase "computer readable medium" refers to storage media readable by a computer, which media may be used to store and retrieve data and software programs incorporating computer code. Exemplary computer readable media include floppy disk, CD-ROM, tape, memory (such as flash memory or system memory), hard drive, and the like.

Thus, the present invention provides a computer readable medium comprising atomic coordinates of an ALDH polypeptide with a ligand bound to a ligand-binding site within the polypeptide. In some embodiments, the atomic coordinates are those set forth in Table 1. In some embodiments, the atomic coordinates are those set forth in Table 6. In some embodiments, a subject computer-readable medium further comprises programming for displaying a molecular model of the ALDH polypeptide with a ligand bound to a ligand-binding site within the polypeptide. In some embodiments, a subject computer-readable medium further comprises programming for identifying a compound that binds to an ALDH polypeptide. For example, the programming for identifying a compound that binds to an ALDH polypeptide can comprise a database of structures of known test compounds.

In another embodiment, the invention provides a computer system having a memory comprising: X-ray crystallographic structure coordinates defining a structure of an ALDH with a bound ligand; and a processor in electrical communication with the memory, wherein the processor generates a molecular model having a three dimensional structure representative of an ALDH with a bound ligand. The processor can be adapted for identifying a candidate compound having a structure that is capable of binding to the ALDH polypeptide.

As used herein, the term "computer system" is understood to mean any general or special purpose system which includes a processor in electrical communication with both a memory and at least one input/output device, such as a terminal. Such a system may include, but is not limited to, personal computers, workstations, and mainframes. The processor may be a general purpose processor or microprocessor or a specialized processor executing programs located in RAM memory. The programs may be placed in RAM from a storage device, such as a disk or preprogrammed ROM memory. The RAM memory in one embodiment is used both for data storage and program execution. The term computer system also embraces systems where the processor and memory reside in different physical entities but which are in electrical communication by means of a network.

The processor executes a modeling program which accesses data representative of an ALDH with a bound ligand. In addition, the processor also can execute another program, a compound modeling program, which uses the three-dimensional model of the ALDH with a bound ligand to identify compounds having a chemical structure that binds to the ALDH. In one embodiment the compound modeling program and the ALDH/bound ligand structure modeling program are the same program. In another embodiment, the compound modeling program and the ALDH/bound ligand structure modeling program are different programs, which programs may be stored on the same or different storage medium. For example, the ALDH/bound ligand structure modeling program may either store the three-dimensional model of ALDH with a bound ligand in a region of memory accessible both to it and to the compound modeling program, or the ALDH/bound ligand model may be written to external storage, such as a disk, CD ROM, or magnetic tape for later access by the compound modeling program.

Compound Libraries for Screening

Inhibitors and/or activators identified according to the methods of the invention can be provided from libraries of compounds available from a number of sources or may be derived by combinatorial chemistry approaches known in the art. Such libraries include but are not limited to the available Chemical Director, Maybridge, and natural product collections. In an exemplary embodiment, libraries of compounds with known or predicted structures may be docked to a subject ALDH/bound ligand structure.

Utility

Compounds identified using a method as described above are useful, for example, in the treatment of a condition or disorder that is amenable to treatment by modulating ALDH activity. Such conditions and disorders include, e.g., conditions involving ischemic stress; chronic free-radical associated diseases; acute free-radical associated diseases; insensitivity to nitroglycerin (e.g., in angina and heart failure); hypertension; diabetes; osteoporosis; cancer; alcohol (e.g., ethanol; ethyl alcohol) addiction; narcotic addiction; aldehyde toxicity; and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Crystal Structure of ALDH2 with Alda-1

Methods

ALDH Expression, Purification, and Kinetic Studies

ALDH2 and ALDH2*2 were produced and purified using an *E. coli* expression system as previously described (Larson et al., 2005, J. Biol. Chem. 280, 30550-30556 and Larson et al., 2007, J. Biol. Chem., 282, 12940-12950). All enzyme assays were performed in 25 mM BES, pH 7.5 and included a final concentration of 2% (v/v) DMSO as a cosolvent in all cases whether or not Alda-1 was present. Enzyme concentrations in the dehydrogenase assays were between 0.03 and 0.06 µM for ALDH2 and between 0.3 and 0.5 µM for ALDH2*2. Esterase assays utilized 0.97 mM para-nitrophenylacetate (pNPA) as a standard substrate concentration and enzyme concentrations for 0.06 µM for ALDH2 and 0.7 µM for ALDH2*2. All kinetic data were analyzed with SigmaPlot (v10.0, StatSys). All activation data for the dehydrogenase and esterase reactions were fit to the expression $v=V_o+\{(V_{max}[S])/(K_{Act}+[S])\}$, where $V_o$ is the initial velocity for the reaction in the absence of activator and $K_{Act}$ is the concentration of activator required for half-maximal activation. All single-vary experiments for Alda-1 activation utilized a minimum of 10 different concentrations across a range from 0-200 µM. The covariation data between NAD⁺ and Alda-1 for ALDH2*2 utilized Alda-1 concentrations between 0-30 µM and NAD⁺ concentrations between 0.5-10 mM and were fit to the nonessential activator equation $v=(V_{max}[S])/\{K_M[(1+[A]/K_A)/(1+\beta[A]/\alpha K_A)]+[S][(1+[A]/\alpha K_A)/(1+\beta[A]/\alpha K_A)]\}$. where [S] is the varied concentration of coenzyme, [A] the varied concentration of activator, α is the modifier on $K_M$, β is the modifier on $V_{max}$ and $K_A$ is the half-maximal concentration of activator. The daidzin inhibition data were fit to the four parameter $EC_{50}$ equation, $v=V_{min}+\{(V_{max}-V_{min})/(1+[S]/EC_{50})^{Hillslope}\}$. All data represent the average of a minimum of three independent experiments with at least two different enzyme preparations.

Crystallization and Structure Determination

Crystals of the wild-type ALDH2 polypeptide (ALDH2*1) or E487K mutant ALDH2 polypeptide (ALDH2*2) were grown under conditions similar to that previously reported (Perez-Miller and Hurley (2003) *Biochem.* 42:7100). Briefly, the apo-enzyme was concentrated to 8 mg/ml and equilibrated against a crystallization solution that contained 100 mM ACES (N-(2-acetamideo)-2-aminoethansulfonic acid), pH 6.4, 100 mM guanidine-HCl, 10 mM MgCl₂, and 16-17% (w/v) poly(ethylene glycol) (PEG) 6000. The complex with Alda-1 was prepared through a direct soaking experiment in which the apo-enzyme crystals were first equilibrated against 1% dimethylsulfoxide (DMSO) in crystal stabilization solution (100 mM ACES, pH 6.4, 100 mM guanidine-HCl, 10 mM MgCl₂, and 19% (w/v) PEG 6000). Following an overnight incubation, the stabilization solution was replaced with an identical solution to which 200 µM Alda-1 was added. The crystals were allowed to soak overnight and prepared for cryogenic freezing, a two-step protocol to introduce 18% (v/v) ethylene glycol into the soaking solution. Diffraction data were collected at beamline 19-ID operated by the Structural Biology Consortium located within the Advanced Photon Source at Argonne National Laboratory. All diffraction data were indexed, integrated, and scaled using the HKL2000/HKL3000 program suite (Otwinowski and Minor (1997) *Meth. Enzymol.* 276:307). X-ray diffraction data and refinement statistics is shown in Table 2.

TABLE 2

| Data Collection†: | ALDH2 | ALDH2*2 |
|---|---|---|
| Space Group | P2₁ | P2₁ |
| Cell Dimensions | a = 102 Å, b = 177 Å, c = 103 Å α = γ = 90°, β = 94.5° | a = 102 Å, b = 177 Å, c = 102 Å α = γ = 90°, β = 94.6° |
| Resolution | 46.0-1.69 Å | 50.0-1.9 Å |
| Total observations | 1,025,775 | 884,944 |
| Unique Reflections | 375,531 | 281,043 |
| Completeness | 93.1% (90.9%)* | 99.3% (100%)# |
| <I>/σ<sub><I></sub> | 11.4 (2.7)* | 9.6 (2.8)# |
| R<sub>merge</sub> | 0.077 (0.27)* | 0.107 (0.40)# |
| Refinement: | | |
| R<sub>free</sub>/R<sub>work</sub> | 0.21/0.25 (0.24/0.32)* | 0.14/0.18 (0.20/0.27)# |
| R.m.s.d. ideal bonds | 0.011 Å | 0.007 Å |
| R.m.s.d. ideal angles | 1.36 Å | 1.09 Å |
| Bound activator molecules | 8 | 8 |
| Bound solvent atoms | 3,135 | 2,731 |

†Data collected at SBC beamline 19-ID, Argonne National Laboratory
*Values for the highest resolution shell (1.74-1.69 Å)
Values for the highest resolution shell (1.93-1.90 Å)

The structure of Alda-1 is as follows:

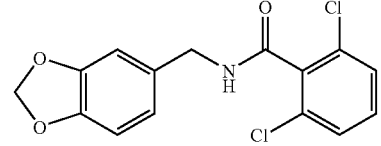

N-(1,3-benzodioxol-5-ylmethyl) -2,6-dichlorobenzamide (Alda-1)

Alda-1 is an ALDH2 agonist. Alda-1 (at 100 µM) increased the activity of the homotetrameric mutant, ALDH2*2 11 fold, the heterotetrameric ALDH2 2.2 fold (similar to the base levels of wild type ALDH2) and the homotetrameric wild type ALDH2*1/*1 2.1 fold (FIG. 2). Chen et al. (2008) *Science* 321:1493-1495; PMID: 18787169.

Crystals of ALDH2 tend to form two different lattice groups: primitive orthorhombic P2₁2₁2₁ and a pseudo-centered monoclinic lattice that indexes in the C222₁ space group with the same cell dimensions as the primitive orthorhombic lattice. However, the intensities of the diffraction pattern lack the strict orthorhombic symmetry and generally require integration in the primitive monoclinic lattice. As the structure is essentially isomorphous with the wild-type ALDH2 monoclinic data set (Zhou et al. (1999) supra), the structure was solved by direct refinement using the wild-type human ALDH2 structure (with ligands and solvent removed) as the starting model (PDB code 1cw3). Confirmation of the binding of Alda-1 (N-(1,3-benzodioxol-5-ylmethyl)-2,6-dichlorobenzamide) was evaluated through inspection of the initial Fo-Fc electron density maps. Refinement of the structures utilized the program Refmac (Murshudov et al. (1997) *Acta Crystallogr. D. Biol. Crystallogr.* 53:240) or Phenix (P. D. Adams et al. (2002) *Acta Cryst.* D58, 1948-1954), and was visually inspected and adjusted using the visualization program Coot (Emsley and Cowtan (2004) *Acta Crystallogr. D. Biol. Crystallogr.* 60:2126).

Results
Structure of Alda-1 Bound to ALDH2

The atomic coordinates of the crystal structure of ALDH2 with Alda-1 are provided in Table 1. The atomic coordinates of the crystal structure of an E487K mutant of ALDH2 with Alda-1 are provided in Table 6.

Figure 3:
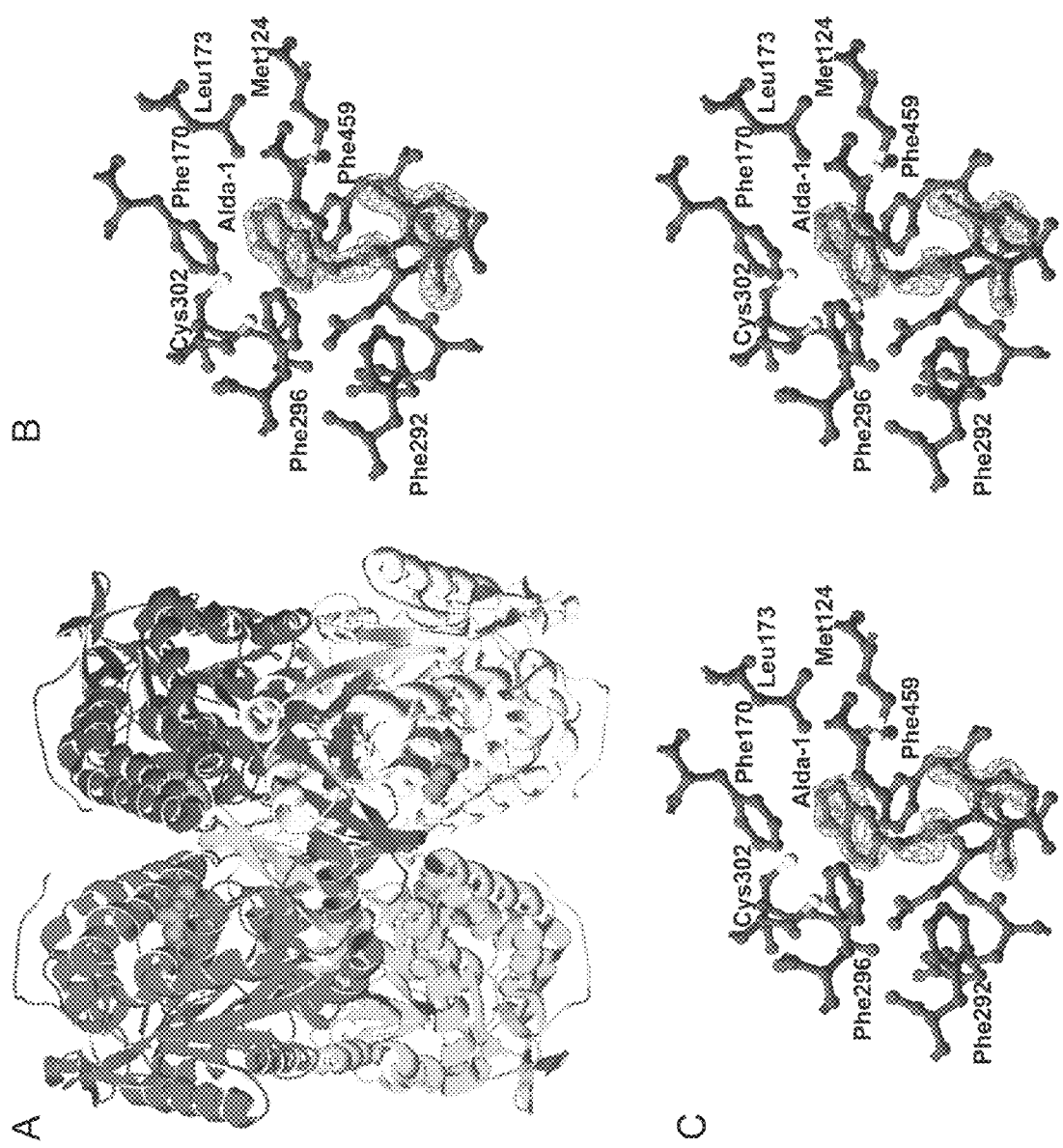
FIGS. 3A-C depict a structure of ALDH2 with Alda-1 bound. (A) Ribbon diagram of the ALDH2 tetramer with different color denoting the individual subunits and the bound Alda-1 molecules indicated using the gray space-filling atom representation. (B) Stereoview of the original Fo-Fc (top, contoured at 3 standard deviations of the map). (C) Final refined 2Fo-Fc electron density (contoured at 1.2 standard deviations of the map) for Alda-1 bound to ALDH2*1. Produced using SPDBViewer and PovRay.
Figure 4:
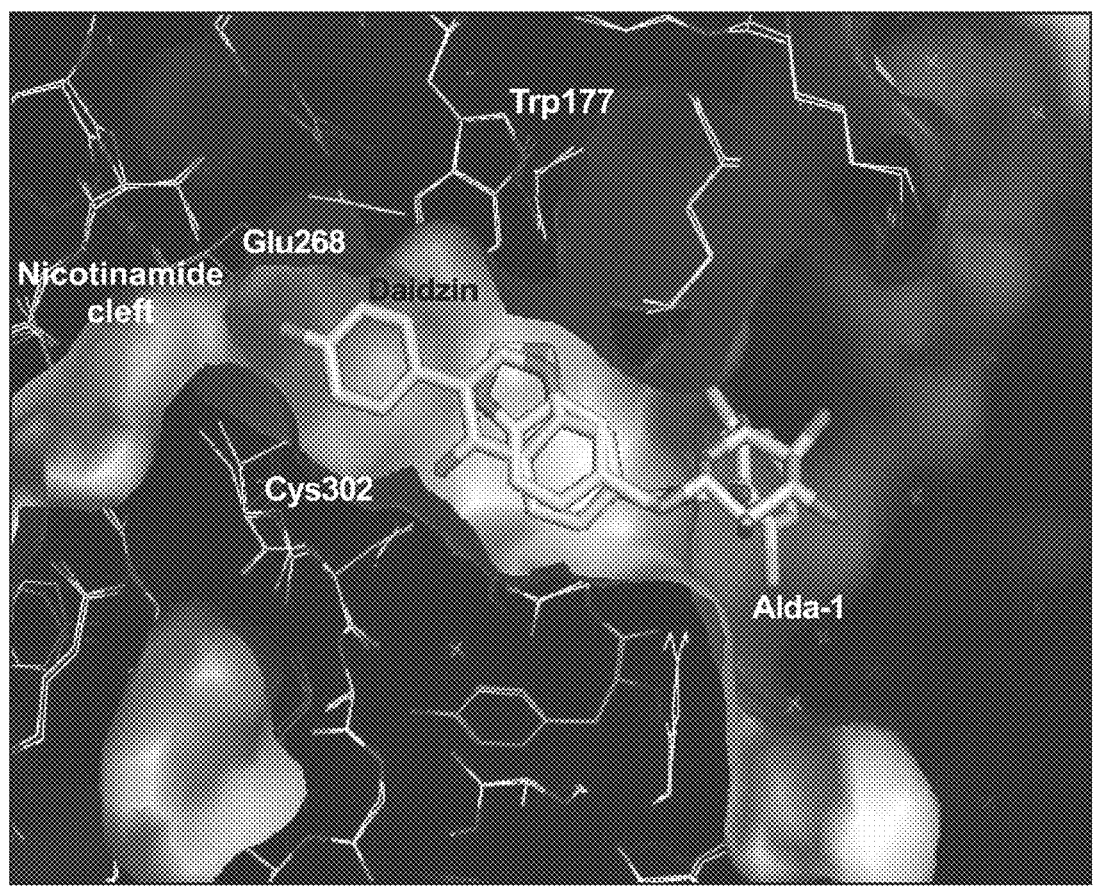
FIG. 4 depicts overlay of the aligned structures of ALDH2 with bound Alda-1 and with bound daidzin (pdb entry 1OF7).

The structure of wild-type ALDH2 in a binary complex with Alda-1 was determined to 1.69 Å and that of the binary complex between Alda-1 and an S302 mutant of ALDH2*2 was determined to 1.9 Å (Table 2). Alda-1 binds to both forms of ALDH2 at the exit of the substrate tunnel and extending in toward the active site (FIGS. 3 and 11), leaving the catalytic Cys302 unimpeded, though it adopts two distinct rotamer positions. The benzodioxol group of Alda-1 is bound within an aromatic and hydrophobic collar comprised of amino acids Val120, Met124, Phe170, Leu173, Phe292, Phe296, and Phe459 solely through hydrophobic interactions. A single highly critical hydrogen bond is formed between the amide nitrogen that links the two ring structures in Alda-1 and the mainchain carbonyl oxygen atom of Asp457. The dichlorobenzamide ring is bound also primarily through hydrophobic interactions between the benzamide ring with Val458, Phe292 and Met124. It is interesting to note that diadzin, an ALDH2 inhibitor, occupies a site that overlaps with Alda-1 (12, PDB code 2VLE). However, the additional phenolic arm of daidzin reaches further into the catalytic site and contacts Cys302 and Glu268, thus blocking catalytic function (FIG. 4). FIG. 4 was generated using PYMOL and atom type coloring is utilized for both structures. The available molecular surface in this region for ALDH2 is displayed using the daidzin structure and the molecule is sliced above the plane of the bound ligands. Critical active site residues are labeled. The cleft through which the nicotinamide moiety accesses the active site lies to the left of Glu268 and Cys302 in this view and is labeled. For the complex between Alda-1 and ALDH2*2, it is important to note that the active site loop comprised of residues 465-477 and the alpha-helix comprised of residues 245-262 are visible in this crystal structure, where these sections of protein structure were disordered in the ALDH2*2 crystal structure reported in the absence of ligands (Larson et al. 2005, supra) (FIG. 10).

Figure 10:
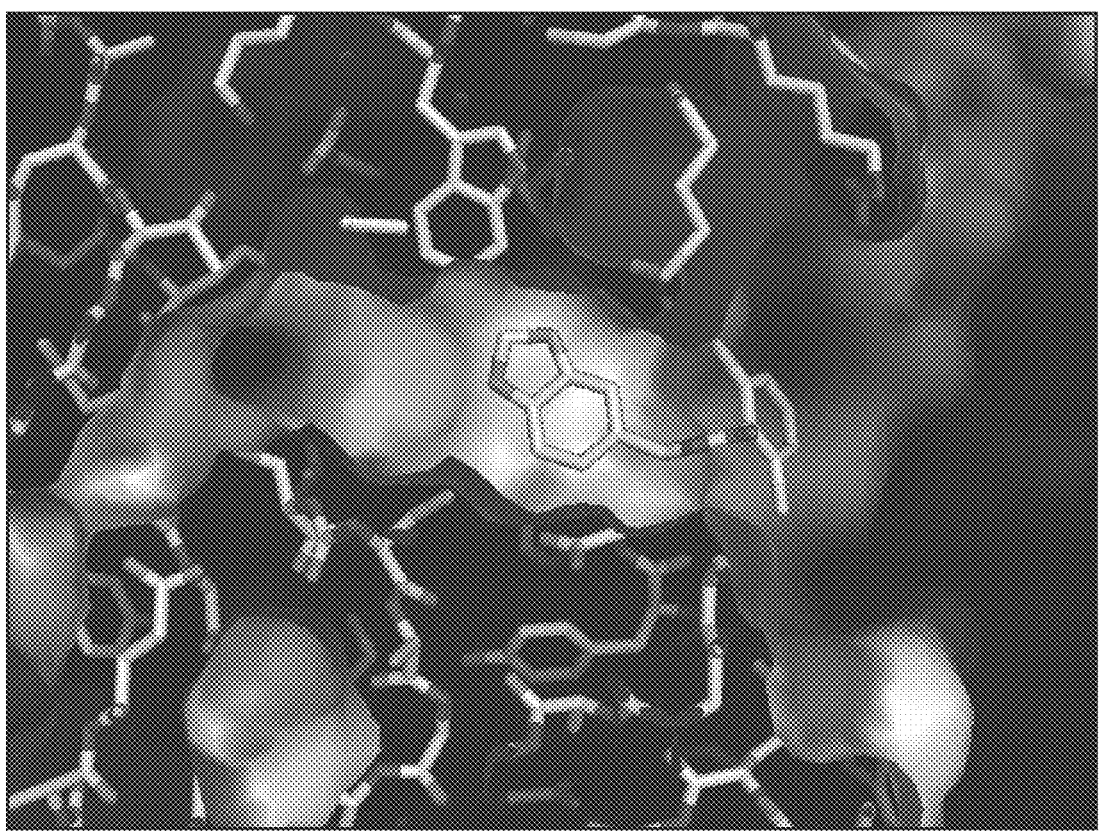
FIG. 10 depicts binding of Alda-1 to ALDH2*2.
Figure 11:
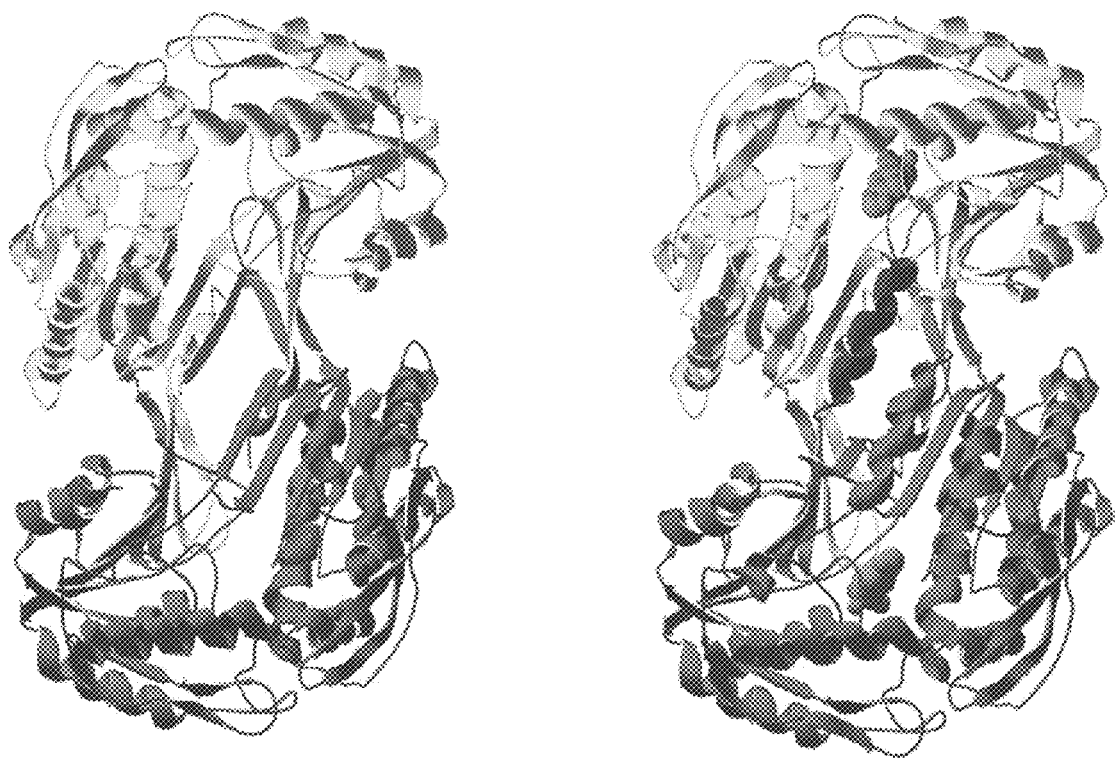
FIG. 11 provides ribbon representations of the structure of ALDH2*2 without (left) and with (right) Alda-1 bound. The helices at the interface between the subunits are restored in the electron density maps when Alda-1 is bound to ALDH2*2 (grey space-filling atoms).

FIGS. 10 and 11. The structure of Alda-1 bound to ALDH2*2 at 1.9 Angstroms resolution shows that Alda-1 binds in the same location as to the wild-type ALDH2 structure (FIG. 10). The binding of Alda-1 to ALDH2*2 restores the coenzyme-binding sites of ALDH2*2 to that more similar to wild-type ALDH2 than to that of ALDH2*2 in the absence of Alda-1 (FIG. 11). Consequently, both the kinetic data and structural data support a mechanism for Alda-1 activation that is based on the partial restoration of ALDH2*2 to a state that is more similar to the wild-type enzyme.

Kinetic Characterization of Alda-1 Activation for the Dehydrogenase Activity of Wild-Type ALDH2 and ALDH2*2

The location of Alda-1 within the substrate-binding tunnel of ALDH2 raises two possibilities: a) the activation effect of Alda-1 is substrate length dependent and b) Alda-1 activation and daidzin inhibition are mutually exclusive. At pH 7.5 a strong dependence of activation on the length and nature of the substrate aldehydes was found, with linear aliphatic aldehydes up to butyraldehyde activated by Alda-1 with μM $K_{Act}$ values (Table 3) and aromatic aldehydes such as benzaldehyde, phenylacetaldehyde and 4-trans-(N,N-dimethylamino)-cinnamaldehylde (DACA) exhibiting minimal effects at 20 μM Alda-1 and saturating concentrations of substrate. Thus, the space between Cys302 and the benzodioxal ring of Alda-1 can accommodate up to 4 carbons in length. As shown in Table 3, smaller linear aliphatic aldehydes were activated by Alda-1 and the extent of activation decreased with length.

TABLE 3

Substrate Dependence for Alda-1 Activation
(25 mM BES, pH 7.5, 0.5 mM NAD$^+$)

| Substrate | $V_{max}^{(app)}$ (min$^{-1}$) | $K_{Act}^{(app)}$ (μM) | $V_m/V_o$ |
|---|---|---|---|
| 100 μM Acetaldehyde | 107 +/− 12 | 0.98 +/− 0.20 | 1.8 +/− 0.1 |
| 100 μM Propionaldehyde | 78.5 +/− 9.6 | 5.1 +/− 1.2 | 1.7 +/− 0.1 |
| 100 μM Butyraldehyde | 86.6 +/− 3.1 | 1.8 +/− 0.5 | 1.3 +/− 0.1 |

Alda-1 had little effect on activity with benzaldehyde, even at the maximum concentration used; 200 μM. Alda-1 also had little effect on ALDH2 activity with phenylaceteldehyde or DACA, although high concentrations of Alda-1 (>100 μM) were weakly inhibitory.

Figure 5A:
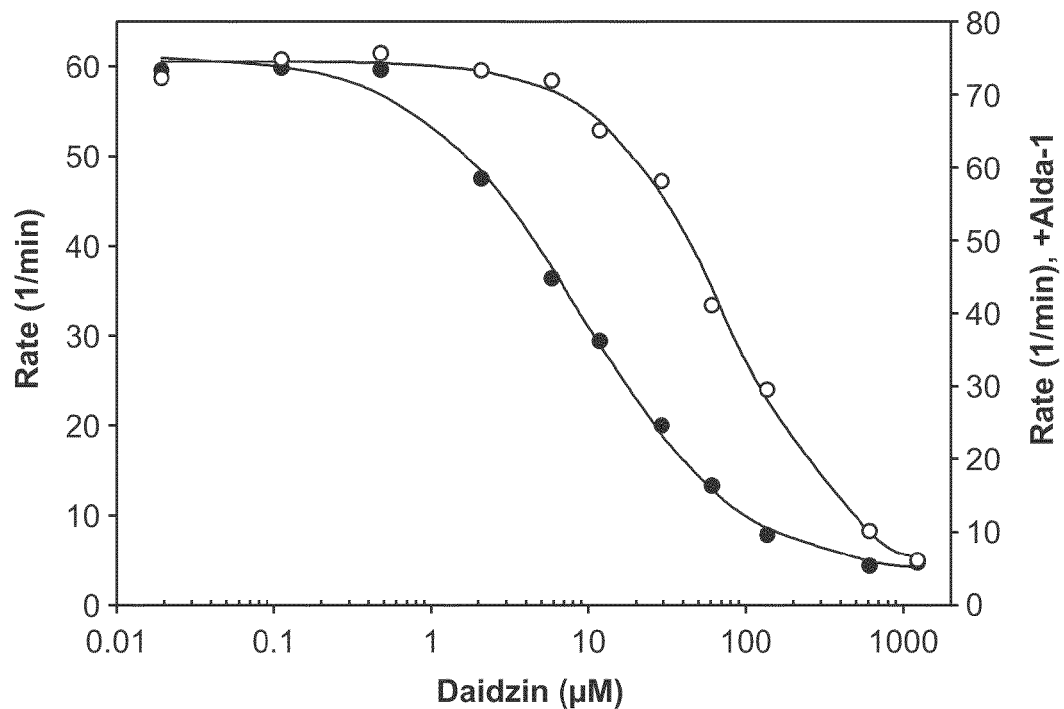
FIGS. 5A and 5B depict Alda-1 competition with daidzin inhibition. Dehydrogenase activity was measured at 0.1 mM propionaldehyde, varying concentrations of daidzin. (A) Wild-type ALDH2 at 0 μM or 10 μM Alda-1 and (B) ALDH2*2 at 0 μM or 50 μM Alda-1. $NAD^+$concentrations were 0.5 mM for wild-type ALDH2 and 10 mM for ALDH2*2. Lines show fits to 4-parameter logistic curve.
Figure 5B:
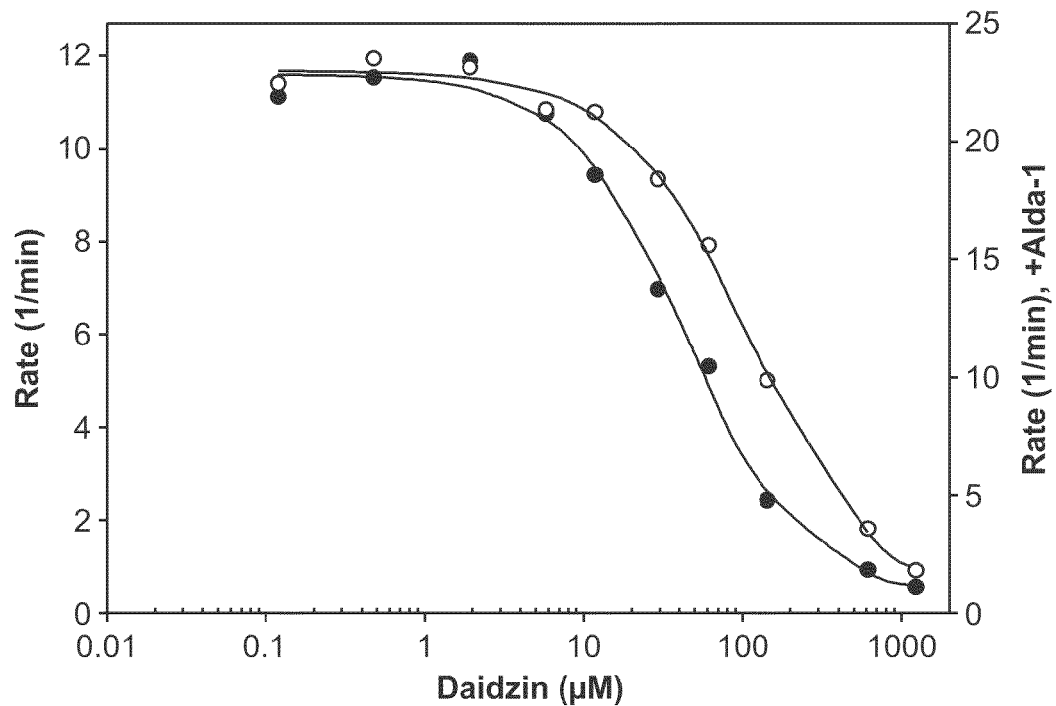

Alda-1 antagonized daidzin inhibition of both ALDH2 and ALDH2*2 in a manner consistent with their overlapping binding sites in ALDH2 (Table 4 and FIG. 5).

TABLE 4

Alda-1 induced antagonism of Daidzin Inhibition
[25 mM BES, pH 7.5, 100 μM propionaldehyde and
0.5 mM NAD$^+$ (ALDH2) or 10 mM NAD$^+$ (ALDH2*2)]

| | ALDH2 (no Alda-1) | ALDH2 (10 μM Alda-1) | ALDH2*2 (no Alda-1) | ALDH2*2 (50 μM Alda-1) |
|---|---|---|---|---|
| $V_{max}^{(app)}$ (min$^{-1}$) | 61.5 +/− 6.1 | 74.9 +/− 12.1 | 11.6 +/− 1.3 | 23.0 +/− 1.7 |
| $V_{min}^{(app)}$ (min$^{-1}$) | 5.1 +/− 4.7 | 2.5 +/− 5.2 | 0.2 +/− 0.6 | 0.2 +/− 0.2 |
| Daidzin IC$_{50}$ (μM) | 8.0 +/− 0.6 | 72.0 +/− 16.9 | 44.8 +/− 10.4 | 113.0 +/− 15.6 |
| Hill Slope | 0.9 +/− 0.3 | 1.0 +/− 0.1 | 1.1 +/− 0.1 | 1.1 +/− 0.1 |

Figure 6:
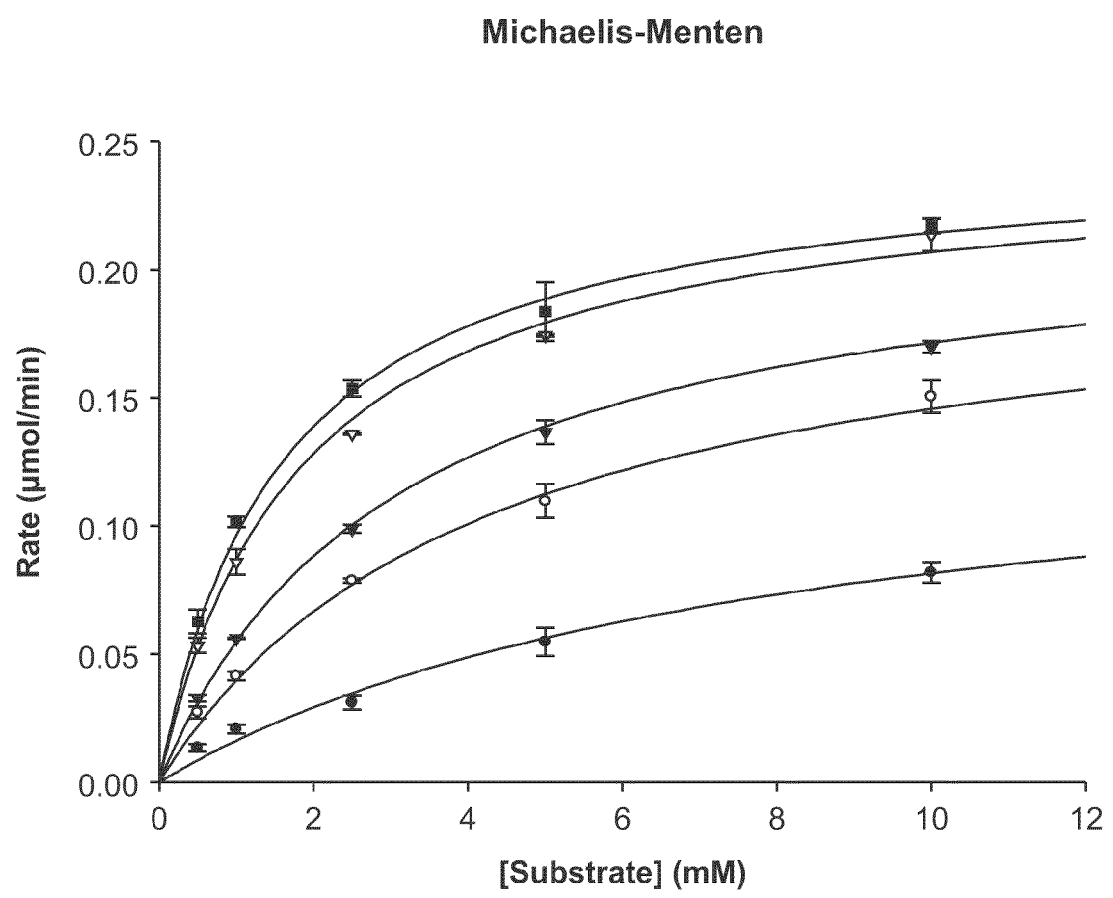
FIG. 6 shows M-M plot for the effects of Alda-1 on the dehydrogenase activity of ALDH2*2 against varied $NAD^+$.

The nature of the activation of ALDH2*2 was analyzed in detail through a covariation experiment between NAD$^+$ and Alda-1 and the data was fitted to the non-essential activator equation. This analysis showed that Alda-1 increases the $V_{max}$ of ALDH2*2 by 2-fold and decreases the apparent Km for NAD$^+$ by 6.7-fold (FIG. 6). The plot in FIG. 6 shows the average values from 3 experiments: $K_{act}$=16±3 μM; $K_M^{NAD}$=7.4±0.7 mM; α-factor=0.15±0.03; β-factor=2.0±0.2. The concentrations of Alda-1 were varied from 0 to 30 μM. The α- and β-factors describe the manner in which Alda-1 impacts the observed $K_M^{NAD}$ and $V_{max}$, respectively. Thus, Alda-1 restores the $K_M$ for NAD$^+$ from 7.4 mM to 1.1 mM and increases the $V_{max}$ 2-fold.

Kinetic Characterization of Alda-1 Activation for the Esterase Activity of Wild-Type ALDH2 and ALDH2*2

In addition to the dehydrogenation reaction, members of the aldehyde dehydrogenase family also exhibit the ability to hydrolyze esters, such as p-nitrophenylacetate, and coenzyme is known to stimulate the hydrolytic activity (Feldman and Weiner, 1972, J. Biol. Chem. 247, 267-272 and Takahashi and Weiner, 1981, Biochemistry 20, 2720-2726). The ability of Alda-1 to stimulate the hydrolysis of p-nitrophenylacetate both in the presence and absence of coenzyme was examined. Alda-1 alone was found to activate the esterase activity of both ALDH2 and ALDH2*2 between 6- and 7-fold and the combined activating effects of both Alda-1 and NAD$^+$ increase ester hydrolysis 10-fold for ALDH2 and over 100-fold for ALDH2*2 (Table 5).

TABLE 5

Esterase Activity Activation Constants for ALDH2 and ALDH2*2
(25 mM BES, pH 7.5, 0.97 mM p-Nitrophenylacetate)

| Constant | ALDH2 | ALDH2 (0.5 mM NAD$^+$) | ALDH2*2 | ALDH2*2 (1.0 mM NAD$^+$) | ALDH2*2 (50 μM Alda-1) |
|---|---|---|---|---|---|
| $V_o$ (min−1) | 24.9 +/− 2.0 | 96.3 +/− 2.2 | 0.40 +/− 0.03 | 1.36 +/− 0.28 | 0.64 +/− 0.19 |
| $V_{max}$ (min$^{-1}$) | 181 +/− 6.8 | 248 +/− 22 | 2.3 +/− 0.2 | 14.7 +/− 1.3 | 49.5 +/− 4.3 |
| $K_{Act}^{(app)}$ (μM) | 3.4 +/− 0.5 | 2.6 +/− 0.1 | 16.1 +/− 5.8 | 11.2 +/− 1.3 | 2,820 +/− 330 |
| $V_{max}$ (min$^{-1}$) | — | 242 +/− 14 | — | — | — |
| $K_i^{(app)}$ (μM) | — | 328 +/− 24 | — | — | — |

At higher concentrations Alda-1 and NAD$^+$ become antagonistic for ALDH2, a behavior not noted for ALDH2*2 at the concentrations examined herein. Similar to that observed for coenzyme-binding kinetics in the dehydrogenation reaction catalyzed by ALDH2*2, Alda-1 lowered the half-maximal activating concentration of NAD$^+$ for the esterase reaction from 7.5 mM (8) to 2.8 mM for ALDH2*2.

Example 2

Use of Model to Predict Ligand Binding

Figure 7:
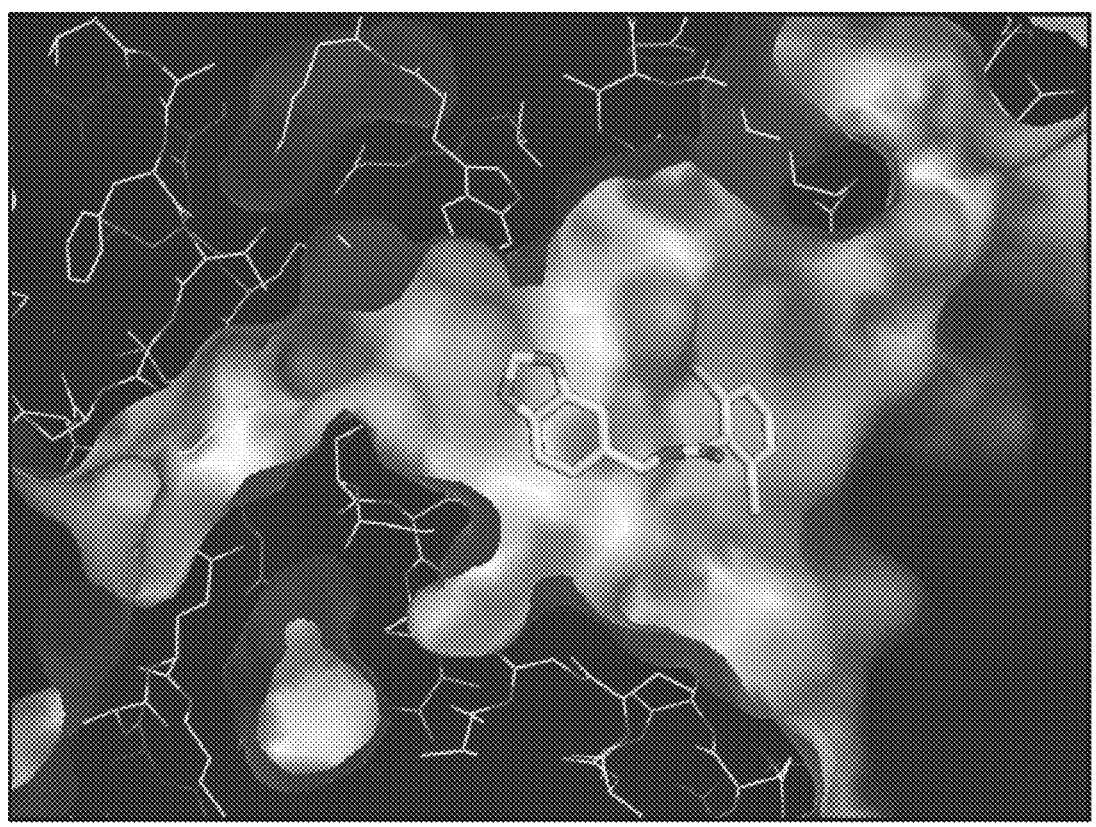
FIG. 7 depicts a substrate-binding site surface of ALDH1A1 with the position of Alda-1 as found in ALDH2 overlayed onto this surface.

A homology model of ALDH5 (now called ALDH1B1) was built. The structures of ALDH3A1 and ALDH1A1 were aligned to that of ALDH2 with Alda-1 bound for significant changes with the residues that contribute to Alda-1 binding.
ALDH1A1b
Within the substrate-binding site of ALDH1A1 (FIG. 7) substitutions of Gly for Met124 and Val for Leu173 enlarges area "A" which will result in the loss of many van der Waals interactions. The substitution of His for Phe292 enlarges site "B" and makes the area more hydrophilic. Lastly the substitution of Val for Phe459, "C", removes a major aromatic stacking interaction with the 1,3-benzodioxol ring and forms a pocket below the ring.

Figure 8:
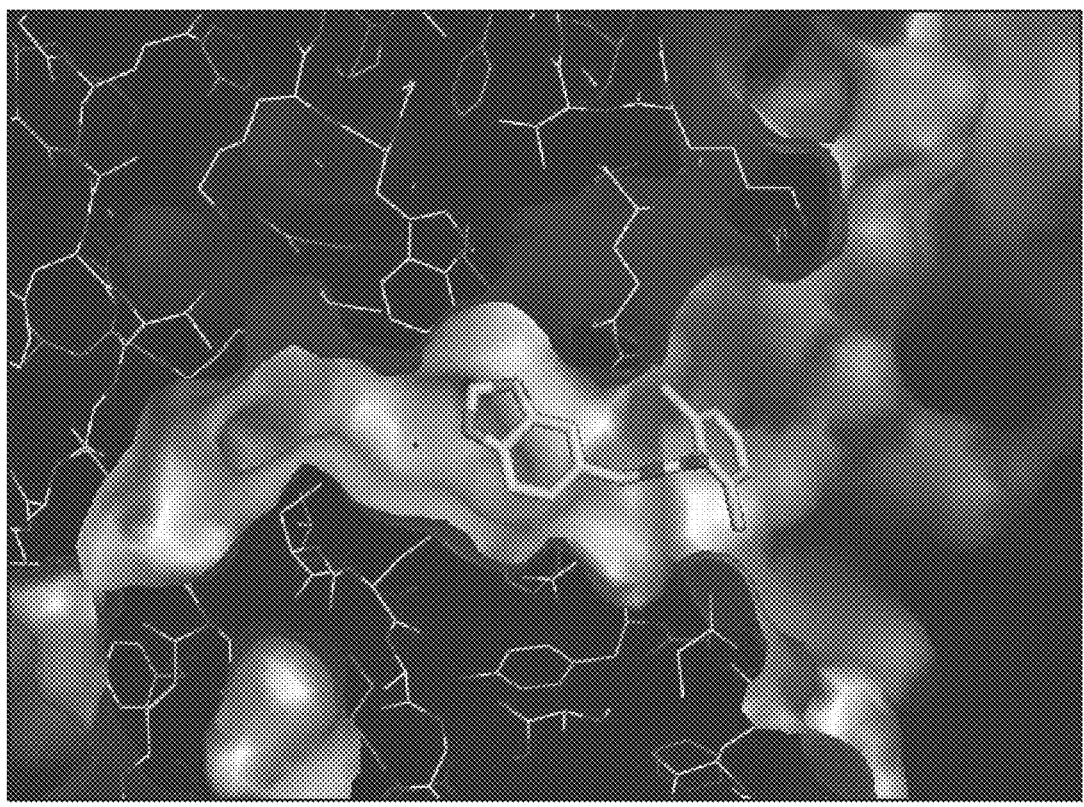
FIG. 8 depicts a substrate-binding site surface of the model of ALDH1B1 with the position of Alda-1 as found in ALDH2 overlayed onto this surface.

Alda-1 is not expected to bind to ALDH1A1 strongly, as the substitutions at positions 124, 173, 292 and 459 greatly increase the available space surrounding Alda-1. The available van der Waals contacts are likely too distantly spaced to support a similar mode of binding.
ALDH1B1
Within the substrate-binding site of ALDH1B1 (FIG. 8) substitutions of Glu for Met124 and Glu for Phe292 create unfavorable electrostatic interactions with the dichlorobenzamide ring. The substitution of Val for Leu173 and Val for Phe459 enlarges the area around the 1,3-benzodioxol ring ("A") and removes a major aromatic stacking interaction and, like ALDH1A1, creates a pocket below the 1,3-benzodioxol ring.

Figure 9:
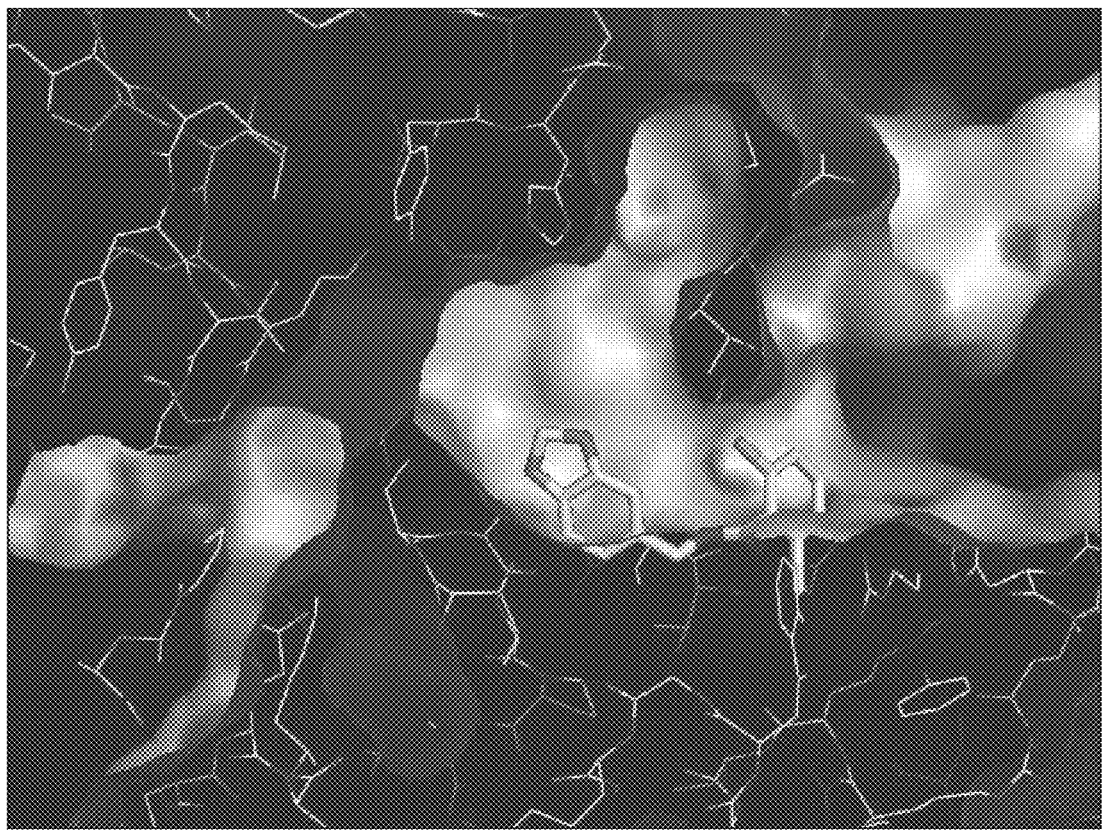
FIG. 9 depicts a substrate-binding site surface of rat ALDH3A1 with the position of Alda-1 as found in ALDH2 overlayed onto this surface.

Alda-1 is not expected to bind to ALDH1B1 strongly, as the Glutamates at positions 124 and 292 create a negatively charge area on both sides of the Alda-1 binding site and the loss of Phe459 removes a major contact surface area under the bicyclic ring of Alda-1.
ALDH3A1
Within the substrate-binding site of ALDH3A1 (FIG. 9) substitutions of Tyr for Met124, the substitution of Trp for Phe292 and a two amino acid insertion at the position equivalent to Phe459 greatly narrows the entry to the substrate-binding pocket (A). In addition, the substitution of Asn for Leu173 and Gln for Trp178 enlarges the area around the 1,3-benzodioxol ring (B). A C-terminal extension present in ALDH3A1 adds additional basic residues, including Arg501 near the exit of the substrate-binding pocket.

The substrate binding site region of ALDH3A1 is very different from ALDH2; it is predicted that Alda-1 would not bind to ALDH3A 1.

The structures of the binary complexes between Alda-1 and ALDH2 and of Alda-1 and ALDH2*2 were solved to 1.69 Å and 1.9 Å resolution. The location of Alda-1 binding within the substrate entrance tunnel of ALDH2 is reminiscent of the binding of daidzin, a known potent inhibitor of ALDH2. If the positions of Alda-1 and daidzin in their respective crystal structures are correct, it was reasoned that Alda-1 should antagonize daidzin inhibition. This was found to be true for both the wild-type ALDH2 and for ALDH2*2, confirming that Alda-1 and daidzin share overlapping binding sites. The very different effects of daidzin and Alda-1 on ALDH2 activity can be explained, in part, from their crystal structures. In the daidzin bound structure, the phenolic moiety interacts directly with two essential active site residues, Cys302 and Glu268, inhibiting the enzyme by restricting substrate binding and catalysis. In contrast, the structure shown herein with ALDH2 and Alda-1 shows that Alda-1 binds at the entrance to the active site, but does not interact with the catalytic residues, leaving Cys302 and Glu268 free to function. Because Alda-1 does block part of the substrate site, it was predicted that ALDH2 activation would depend on substrate size. Modeling of the complex suggests that the space between Cys302 and the benzodioxol ring of Alda-1 could accommodate acyl-enzyme intermediates up to 4 carbons in length. The concentration dependence of Alda-1 activation at saturating concentrations of acetaldehyde, propionaldehyde, butyraldehyde, benzaldehyde, phenylacetaldehyde, and 4-trans-(N,N-dimethylamino)-cinnamaldehyde (DACA) was examined. It was found that only the smaller linear aliphatic aldehydes were activated by Alda-1 and the extent of activation decreased with length. Alda-1 had little effect on activity with benzaldehyde, even at the maximum concentration used; 200 μM. Alda-1 also had little effect on ALDH2 activity with phenylacetaldehyde or DACA, although high concentrations of Alda-1 (>100 μM) were weakly inhibitory.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A crystal comprising an aldehyde dehydrogenase (ALDH) polypeptide bound to a chemical entity, wherein the ALDH polypeptide consists of the amino acid sequence of amino acids 18-517 of SEQ ID NO:1, the chemical entity is N-(1,3-benzodioxol-5-ylmethyl)-2,6-dichlorobenzamide, and the crystal is in the space group $P2_1$ and has unit cell dimensions of a=102 Å, b=177 Å, c=103 Å, $\alpha=\gamma=90°$ and $\beta=94.5°$.

2. A composition comprising the crystal of claim 1.

3. The composition of claim 2, wherein the crystal diffracts x-rays for a determination of structure coordinates to a resolution of 1.69 Angstroms.

4. A crystal comprising an aldehyde dehydrogenase (ALDH) polypeptide bound to a chemical entity, wherein the ALDH polypeptide consists of the amino acid sequence of amino acids 18-517 of SEQ ID NO:1, except Glu at position 504 of SEQ ID NO:1 is replaced with Lys, the chemical entity is N-(1,3-benzodioxol-5-ylmethyl)-2,6-dichlorobenzamide, and the crystal is in the space group $P2_1$ and has unit cell dimensions of a=102 Å, b=177 Å, c=102 Å, $\alpha=\gamma=90°$ and $\beta=94.6°$.

5. A composition comprising the crystal of claim 4.

6. The composition of claim 5, wherein the crystal diffracts x-rays for a determination of structure coordinates to a resolution of 1.9 Angstroms.

\* \* \* \* \*

UNITED STATES PATENT AND TRADEMARK OFFICE
CERTIFICATE OF CORRECTION

PATENT NO.        : 8,124,389 B2
APPLICATION NO.   : 12/435265
DATED             : February 28, 2012
INVENTOR(S)       : Che-Hong Chen Page 1 of 1

It is certified that error appears in the above-identified patent and that said Letters Patent is hereby corrected as shown below:

In the Specification, Col. 1, lines 14-16; should read;

--STATEMENT REGARDING FEDERALLY SPONSORED RESEARCH

This invention was made with Government support under contracts AA011982, AA011147, and AA018123 awarded by the National Institutes of Health. The Government has certain rights in this invention.--

Signed and Sealed this
Tenth Day of July, 2012

David J. Kappos
*Director of the United States Patent and Trademark Office*